(12) United States Patent
Gunzburg et al.

(10) Patent No.: US 7,074,398 B1
(45) Date of Patent: Jul. 11, 2006

(54) RETROVIRAL VECTORS CARRYING SENESCENT CELL DERIVED INHIBITORS 1 (SDI-1)OR ANTISENSE SDI-1 NUCLEOTIDE SEQUENCES

(75) Inventors: Walter H. Gunzburg, Mölding (AT); Robert M. Saller, München (DE); Brian Salmons, Ainhofen (DE)

(73) Assignee: GSF-Forschungszentrum Fuer Umwelt und Gesundheit GmbH, Neuherberg (DE)

( * ) Notice: Subject to any disclaimer, the term of this patent is extended or adjusted under 35 U.S.C. 154(b) by 0 days.

(21) Appl. No.: 09/058,546

(22) Filed: Apr. 10, 1998

Related U.S. Application Data

(63) Continuation of application No. PCT/US96/04447, filed on Oct. 11, 1996.

(30) Foreign Application Priority Data

Oct. 13, 1995 (DK) ..................................... 1157/95

(51) Int. Cl.
*A61K 35/00* (2006.01)
*C12N 15/85* (2006.01)

(52) U.S. Cl. .................. 424/93.2; 424/93.1; 424/93.21; 435/325

(58) Field of Classification Search .................. 514/44; 536/23.1; 424/93.1, 93.2, 93.21; 435/320.1, 435/325, 440, 455
See application file for complete search history.

(56) References Cited

U.S. PATENT DOCUMENTS 5,863,904 A * 1/1999 Nabel et al. ................... 514/44

FOREIGN PATENT DOCUMENTS

| WO | WO 93/12251 | 6/1993 |
| WO | WO 94/29437 | 12/1994 |
| WO | WO 95/06415 | 3/1995 |
| WO | WO 95/13375 | 5/1995 |
| WO | WO 96/07748 A1 | 3/1996 |
| WO | WO 9607748 A1 * | 3/1996 |
| WO | WO 97/09440 | 9/1996 |

OTHER PUBLICATIONS

Feldman et al. Fundamental & Clinical Pharmacology, vol. 9, pp. 8-16, 1995.*
Crystal Science, vol. 270, p. 404-410, 1995.*
Tsang et al. Vaccine Res., vol. 3, p. 183-193), 1994.*
Haertig et al. J. Virology, vol. 67, pp. 813-821, 1993.*
Nakanishi et al. EMBO Journal, vol. 14, pp. 555-563, 1995.*
Miller et al. Biotechniques, vol. 7, pp. 980-990, 1989.*
Price et al. PNAS, USA, vol. 84, pp. 156-160, 1987.*
Noda et al. Exp. Cell Res., vol. 211, pp. 90-98, 1994.*
Stange et al. Biomat. Art. Cells and Immob. Biotech., vol. 21, pp. 343-352, 1993.*

Definition of antisense DNA from Stedman's Medical Dictionary.*
Bond, J.A., et al., "Mutant p53 Rescues Human Diploid Cells from Senescence without Inhibiting the Induction of SDI1/WAF1", *Can. Res.*, 55:2404-2409 (1995).
Katayose, D., et al., "Consequences of p53 Gene Expression by Adenovirus Vector on Cell Cycle Arrest and Apoptosis in Human Aortic Vascular Smooth Muscle Cells", *Biochem. Biophysic. Res. Comm.*, 215 (2) :446-451 (1995).
Skotzko, M., et al., Retroviral Vector-mediated Gene Transfer of Antisense Cyclin G1 (CYCG1) Inhibits Proliferation of Human Osteogenic Sarcoma Cells, *Can. Res.*, 55:5493-5498 (1995).
Nakanishi, M., et al., "Exit from $G_0$ and entry into cell cycle of cells expressing $p21^{Sdi1}$ antisense RNA", *Proc. Natl. Acad. Sci. USA*, 92:4352-4356 (1995).
Zakut, R., "The tumor suppression function of $p21^{Waf}$ is contained in it N-terminal half ('half-WAF')", *Oncog.*, 11:393-395 (1995).
Johnson, M., et al., "Evidence for a p53-Independent Pathway for Upregulation of SDI1/CIP1/WAF1/p21 RNA in Human Cells", *Mol. Carcin.*, 11:59-64 (1994).
Rubelj, I. and Pereira-Smith, O.M., "SV40-Transformed Human Cells in Crisis Exhibit Changes That Occur in Normal Cellular Senescence", *Exper. Cell Res.*, 211:82-89 (1994).
Harper, J.W., et al., "The p21 Cdk-Interacting Protein Cip1 Is a Potent Inhibitor of G1 Cyclin-Dependent Kinases", *Cell*, 75:805-816 (1993).
El-Deiry, W.S., et al., "WAF1, a Potential Mediator of p53 Tumor Suppression", *Cell*, 75:817-825 (1993).
Xiong, Y., et al., "p21 is a universal Inhibitor of cyclin kinases", *Nature*, 366:701-704 (1993).
Hunter, T., "Braking the Cycle", *Cell*, 75:839-841 (1993).
Günzburg, W.H., et al., "A Mammary-Specific Promoter Directs Expression of Growth Hormone not only to the Mammary Gland, but also to Bergman Glia Cells in Transgenic Mice", *Mol. Endocrin.*, 5(1) :123-133 (1991).
U.S. Appl. No. 08/808,827, Gunzburg et al.
Genbank® Accession No. J02255.
Genbank® Accession No. SYNMMLPLN2.
Genbank® Accession No. SYNMMLPLN3.
Genbank® Accession No. SYNMMLPLN4.

* cited by examiner

*Primary Examiner*—Michael Wilson
(74) *Attorney, Agent, or Firm*—Jenkins, Wilson, Taylor & Hunt, P.A.

(57) ABSTRACT

The present invention relates to retroviral vectors carrying DNA sequences encoding SDI-1, function analogues of SDI-1, or fragments thereof, or antisense SDI-1 DNA sequences, and especially retroviral vectors carrying the SDI-1 or antisense SDI-1 sequences under the transcriptional control of target cell specific regulatory elements or promoters or X-ray inducible promoters. Further, the invention relates to the use of such retroviral vectors for the production of recombinant retroviral particles useful for the treatment of disorders or diseases responsive to the antiproliferative activity of SDI-1, or the proliferative activity of antisense SDI-1 sequences.

28 Claims, 13 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: other nucleic acid (A) DESCRIPTION: /desc = "DNA"

(xi) SEQUENCE DESCRIPTION: SEQ ID NO:1:

ATGAAAGACC CCGCGGACGC GTGCGCCAGT CCTCCGATTG A        41

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:2:

TCAATCACTC AGAGGAGACC                                20

(2) INFORMATION FOR SEQ ID NO:3:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:3:

ACATCGATAG AAAAAGGGGG GAATGAAAGA CCCCGCGGAC G        41

(2) INFORMATION FOR SEQ ID NO:4:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:4:

ATACCGCGGA AAAGGGGGA AATGCC                          26

(2) INFORMATION FOR SEQ ID NO:5:

(i) SEQUENCE CHARACTERISTICS:
         (A) LENGTH: 33 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:5:

GCGGCGACGC GTAAGTTTAC TCAAAAAATC AGC                 33

(2) INFORMATION FOR SEQ ID NO:6:

(i) SEQUENCE CHARACTERISTICS:
         (A) LENGTH: 28 base pairs
         (B) TYPE: nucleic acid
         (C) STRANDEDNESS: single
         (D) TOPOLOGY: linear -continued

```
        (ii) MOLECULE TYPE: other nucleic acid
             (A) DESCRIPTION: /desc = "DNA"

(xi) SEQUENCE DESCRIPTION: SEQ ID NO:6:

TATGGACGTC TCCCTGCCGA AGTCAGTT                                           28

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "DNA"

(xi) SEQUENCE DESCRIPTION: SEQ ID NO:7:

TATGGGATCC GGCAGAAGAT GTAGAGCG                                           28
```

RETROVIRAL VECTORS CARRYING SENESCENT CELL DERIVED INHIBITORS 1 (SDI-1) OR ANTISENSE SDI-1 NUCLEOTIDE SEQUENCES

RELATED APPLICATIONS

This application is a Continuation application of PCT/EP96/04447 filed Oct. 11, 1996 which claims priority to DK 1157/95 filed Oct. 13, 1995. The contents of PCT/EP96/04447 and DK 1157/95 are incorporated herein by reference in their entirety.

BACKGROUND OF THE INVENTION

Dividing cells undergo a cyclical programmed that culminates in cell division. A normal event in this cell cycle programmed is the replication of the cellular DNA. Just prior to DNA synthesis, there is a pause to allow proof reading of the DNA, ensuring that any damage or mutations are repaired and not passed on to daughter cells. This checkpoint (GI) is regulated by programmed gene expression. A second, similar checkpoint occurs later on after DNA synthesis, just before the cell divides into two new cells, presumably for the same purpose. Senescent or aged cells are permanently arrested at one of these checkpoints. Recently, Olivia Pereira-Smith, Jim Smith and colleagues have identified three cDNA's that cause growth arrest when transfected into young, actively dividing cells (Noda, A., et al., *Exp. Cell. Res.*, 211:900–98 (1994)). Other groups have described SDI-1 as WAF1, CIP1; PIC1 and p21 (Harper, J. N., et al., *Cell*, 75:805–816 (1993); El-Deiry, W. S. et al., *Cell*, 75:817–825 (1993); Xiong, Y., et al., *Nature*, 366: 701–704 (1993); Hunter, T. et al., *Cell*, 75:839–841 (1993)). This gene plays a central role in cellular processes that have in common the loss of cell proliferation which implicates this gene as being involved in cell cycle control. SDI-1 has been shown to be overexpressed in senescent cells, quiescent cells or cultured primary cells undergoing crisis (Noda, A., et al., *Exp. Cell Res.*, 211:900–98 (1994); Rubelj, I. and Pereira-Smith, O. M., *Exp. Cell Res.* 211:82–89 (1994)), suggesting a role in the maintenance of DNA synthesis inhibition (Johnson, M., et al., *Mol. Carcinogen.*, 11:59–64 (1994)). Further, evidence has been presented suggesting that the SDI-1 medicated inhibition of DNA synthesis occurs via an inhibition of CDK (cyclin-dependent kinases) activity (Nakanishi, M., et al., *Proc. Natl. Acad. Sci. USA*, 92:4352–4356 (1995)). These findings, together with the demonstration that SDI-1 can inhibit cell growth of young dividing cells, suggests that this gene will be useful for gene therapy to inhibit the growth of rapidly proliferating cells in diseases or disorders such as restenosis, in which smooth muscle cells inappropriately divide, or various cancers.

In this respect, SDI-1 will be useful therapeutically to suppress the rapid proliferation of tumor or tumorigenic cells, such as breast, lung, hepatic and glioma tumor cells. SDI-1 has also been described to have the ability to mediate the differentiation of cancer cells (malignant melanoma cells) into non-cancerous cells. Additional applications for SDI-1 in a therapeutic context include the inhibition of endothelial cell replication (antiangiogenesis) to prevent neovascularizations of tumors, and to halt cell growth (WO-Al-95 06415).

SDI-1 induces a senescent or quiescent state in recipient cells and will therefore also be useful in the treatment of various age-related disorders, asthenia and cachexia, or other diseases or conditions in which rapid cellular proliferation is undesirable.

SDI-1 can also be used in combination with conventional chemotherapeutic agents in order to enhance the efficacy of chemotherapeutic agents. The premise of chemotherapy is that cancer cells grow more rapidly than normal cells, and hence are more sensitive to cytotoxic agents than normal cells. Many chemotherapeutic agents exert their effect during a specific phase or set of phases of the cell cycle, and because only a fraction of tumor cells are in a specific phase at any given time, such drugs must generally be provided by repeated administration.

SDI-1 can be used to synchronize or maximize the percentage of cells that are in a particular phase of the cell cycle at the time of administering the chemotherapeutic agent, and thereby provide a means to increase the effectivity of chemotherapy.

Other diseases such as psoriasis, rheumatoid arthritis and restenosis can also be treated with SDI-1. The use of SDI-1 for the treatment of viral and microbial infections and several other disorders or diseases are described in WO-Al-95/06415.

Antisense sequences are nucleic acids (either DNA or RNA) whose sequence is complementary to the sequence of a target mRNA molecule (or its corresponding gene) so that it is capable of hybridizing with binding to the mRNA molecule (or gene) and thereby impairing (i.e. attenuating or preventing) the transcription of the gene into mRNA or the translation of the mRNA molecule into a gene product.

Antisense SDI-1 DNA sequences may thus be used to inhibit the production of endogenous SDI-1 and thereby stimulate the proliferation of cells. Antisense SDI-1 DNA sequences may therefore be used to promote wound healing, angiogenesis, endothelial cell proliferation, recovery from burns or surgery or to restore attrophied tissue (WO-Al-95 06415). Antisense SDI-1 DNA sequences can also be used to immortalize cells and permit the establishment of permanent cell lines. Antisense SDI-1 DNA sequences may also be used in research or to permit or facilitate the accumulation of large numbers of cells, as for organ tissue grafts or transplants, or they may be used to immortalize cells producing important biological molecules such as hormones, interferons, or growth factors.

Transcription of antisense SDI-1 DNA sequences in cells in combination with irradiation leads to an increase in cell death. Transcription of antisense SDI-1 DNA sequences may therefore also be useful for gene therapy for the treatment of diseases or disorders characterized by rapid cell proliferation, such as certain tumors as well as in vascular diseases such as restenosis.

Retroviral vectors are suitable gene transfer vehicles for stable therapeutic gene delivery to rapidly dividing cells such as cancer cells, becuase most retroviral particles only infect dividing cells and not the surrounding non-dividing cells. Further, the retroviral vector integrates in the chromosomal DNA of dividing cells, thereby ensuring the transmission of therapeutic genes to all daughter cells, if the original infected cell is proliferating. Retroviral vectors are therefore the ideal vector for the delivery of DNA sequences encoding polypeptides affecting the proliferation of cells, such as SDI-1, into cells.

SUMMARY OF THE INVENTION

It is an object of the present invention to provide retroviral vectors expressing SDI-1 DNA sequences, functional analogues, or fragments thereof, useful for the inhibition of cell proliferation, as well as retroviral vectors carrying antisense SDI-1 DNA sequences useful for enhancing cell proliferation.

It is a further object of the present invention to provide such retroviral vectors wherein the SDI-1 DNA sequences, functional analogues, or fragments thereof, or antisense SDI-1 DNA sequences are under the transcriptional control of target cell specific regulatory elements or promoters, especially mammary cell specific regulatory elements or promoters, or X-ray inducible promoters.

Another object of the present invention is to provide recombinant retroviral particles capable of delivering SDI-1 sequences, functional analogues, or fragments thereof, or antisense SDI-1 sequences to cells, and the use thereof for the treatment of disorders or diseases characterized by rapidly proliferating cells, such as cancer and restenosis.

DETAILED DESCRIPTION OF THE INVENTION

Figure 1:
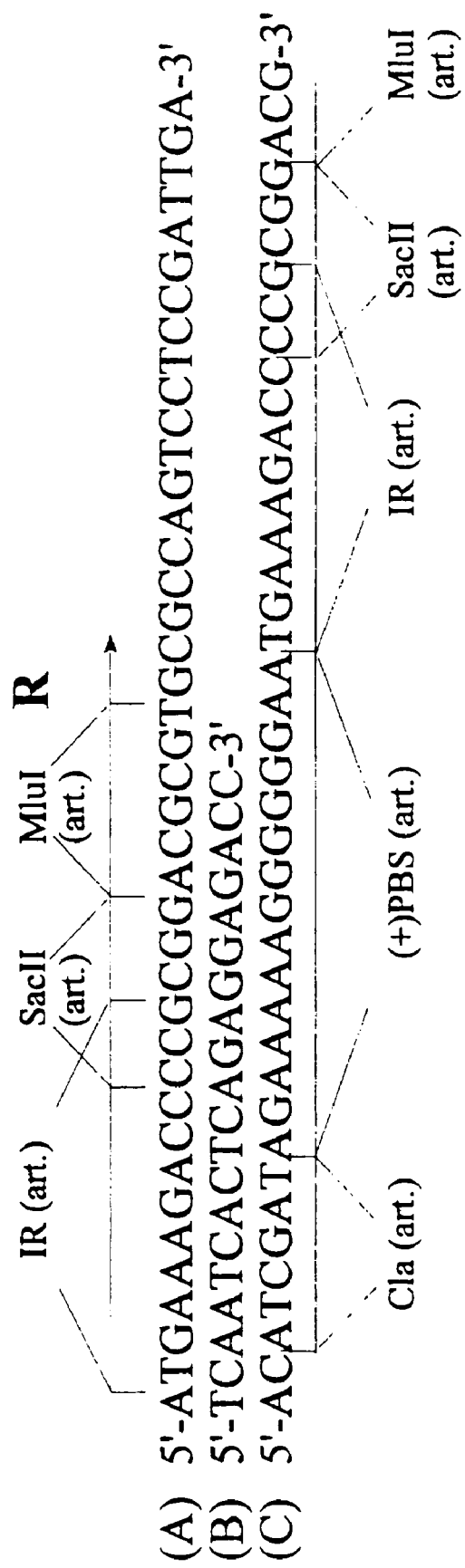
FIG. 1: Primers A (SEQ ID NO: 1), B (SEQ ID NO: 2), and C (SEQ ID NO: 3) used for deletion of U3 of MLV and insertion of a SacII-Mlu polylinker in its place.

The invention then, inter alia, comprises the following, alone or in combination:

A replication defective retroviral vector carrying a DNA sequence encoding SDI-1, a functional analogue, or a fragment thereof, or an antisense SDI-1 DNA sequence;

a retroviral vector as above carrying a DNA sequence encoding SDI-1;

a retroviral vector as above wherein the DNA sequence codes for amino acids 1 to 71 of SDI-1;

a retroviral vector as above wherein the DNA sequence codes for amino acids 42 to 58 of SDI-1;

a retroviral vector as above carrying a DNA sequence which is antisense to the SDI-1 gene;

a retroviral vector as above wherein the antisense SDI-1 DNA sequence is 10 to 30, preferably 15 to 24 nucleotides long and prepared according to the nucleotide sequence of the SDI-1 gene;

a retroviral vector as above wherein the antisense SDI-1 DNA sequence is antisense to nucleotides 75 to 93 of the DNA sequence encoding SDI-1;

a retroviral vector as above, wherein the vector comprises a 5' LTR region of the structure U3-R-U5; one or more sequences selected from coding and non-coding sequences; and a 3' LTR region comprising a completely or partially deleted U3 region wherein said deleted U3 region is replaced by a polylinker sequence containing a regulatory element or a promoter, followed by the U5 and R region, characterized in that at least one of the coding sequences is a DNA sequence encoding SDI-1, a functional analogue thereof, or a fragment thereof, or an antisense SDI-1 DNA sequence which is under transcriptional control of said regulatory element or promoter;

a retroviral vector as above wherein the DNA sequence encoding SDI-1, a functional analogue, or a fragment thereof, or the antisense SDI-1 DNA sequence is under transcriptional control of a target cell specific regulatory element or promoter or an X-ray inducible promoter;

a retroviral vector as above wherein the target cell specific regulatory element is selected from the WAP and MMTV regulatory elements;

a retroviral vector as above which is pLXS-SDI1;

a retroviral vector as above which is pLX125.IDS;

a packaging cell line harbouring;
a) a retroviral vector as above;
b) at least one DNA construct coding for the proteins required for said retroviral vector to be packaged;

a packaging cell line as above which is of human origin;

encapsulated cells comprising a core containing packaging cells as above and a porous capsule wall surrounding said core, said porous capsule wall being permeable to the retroviral particles produced by said packaging cells;

encapsulated cells as above wherein said porous capsule wall consists of a polyelectrolyte complex formed from counter charged polyelectrolytes;

a recombinant retroviral particle produced by culturing a packaging cell line as above harbouring a retroviral vector carrying a DNA sequence encoding SDI-1, a functional analogue, or a fragment thereof, under suitable conditions optionally followed by isolation of the recombinant retroviral particle produced;

a recombinant retroviral particle produced by culturing a packaging cell line as above harbouring a retroviral vector carrying an antisense SDI-1 DNA sequence under suitable conditions optionally following by isolation of the recombinant retroviral particle produced;

a pharmaceutical composition comprising a recombinant retroviral particle as above and a pharmaceutically acceptable carrier or diluent;

a pharmaceutical composition comprising a packaging cell line as above and a pharmaceutically acceptable carrier or diluent;

the use of a retroviral particle as above for the preparation of a medicament for the treatment of disorders or diseases responsive to the anti-proliferative activity of SDI-1;

the use as above of the preparation of a medicament for the treatment of a cancer, or restenosis;

the use as above for the preparation of a medicament for the treatment of breast cancer;

the use of a retroviral particle as above for the preparation of a medicament for the treatment of a disorder or disease responsive to the proliferation activity of antisense SDI-1 DNA sequences;

the use as above for the preparation of a medicament for the treatment of cancer;

a method for introducing DNA sequences encoding SDI-1, a functional analogue, or a fragment thereof or an antisenses SDI-1 sequence into human cells in vitro or in vivo comprising infecting a target cell population with a retroviral particle as above;

a method for the treatment of a disorder or disease responsive to the antiproliferative activity of SDI-1 comprising administering to a living animal body, including a human, in need thereof a therapeutically effective amount of a retroviral particle as above;

a method as above wherein the disorder or disease is a cancer, or restenosis;

a method for the treatment of a disorder or disease responsive to the proliferative activity of antisense SDI-1 sequences comprising administering to a living animal body, including a human, in need thereof a therapeutically effective amount of a retroviral particle as above;

a method as above wherein the disorder or disease is cancer, and the administration of the retroviral particle is combined with irradiation; and a method as above wherein the recombinant retroviral particle is administered as an injection, or by implantation of a packaging cell line as above, or an encapsulated packaging cell line as above into the living animal body, including a human, nearby or at the site of the tumor.

The DNA sequence and the amino acid sequence of SDI-1 is described in WO-Al-95 06415. Active domains of SDI-1 are also described herein:

The SDI-1 polypeptide is 164 amino acids long, but deletion of the carboxy terminal portion of the SDI-1 molecule (amino acids 72–164) do not significantly affect the inhibitory effect of the polypeptide. The active domains of SDI-1 are therefore present within a peptide fragment containing amino acids 1 to 71. Active domains also comprise amino acids 42 to 47, 53 to 58 and 66 to 71. Deletion of amino acids 53 to 58 was found to result in the greatest loss of DNA synthesis inhibitory activity (50% of full length DNA). Deletions of amino acids 42 to 47 and 66 to 71 also resulted in a loss of inhibitory activity but to a much lesser extent. Deletion analysis have thus indicated that the critical region of SDI-1 polypeptide must be between amino acids 42 to 71, and fine studies implicate that the region between amino acids 48 to 65 are critical for the negative growth effects of the gene.

Fragments of SDI-1 having a function of biological activity analogous to that of SDI-1 thus include the first 70 amino acids of SDI-1. Smaller fragments such as those containing SDI-1 amino acid residues: 5–70, 10–70, 15–70, 20–70, 25–70, 30–70, 35–70 or 40–70 and especially amino acids 42 to 71 may also be employed. Such fragments can easily be identified by cleaving SDI-1 nucleic acid molecules by mechanical or preferably restriction endonuclease cleavage and thereby generate candidate fragments. Such fragments can then be provided to cells, and their capacity to inhibit DNA synthesis can be monitored.

Functional analogues of SDI-1 means analogues of SDI-1 which are chemically related to SDI-1 and have a function or biological activity analogous to that of SDI-1. Such analogues include naturally and non-naturally occurring derivatives of SDI-1.

Non-naturally occurring functional analogues of SDI-1 can be identified by random mutation or site directed mutagenesis. Random mutation of target gene sequences to obtain mutant proteins having the desired characteristics have been described previously (Leatherbarrow, R. J., *Prot. Eng.*, 1:7–16 (1986); Knowles, J. R., *Science* 236:1252–1258 (1987); Shaw, W. N., *Biochem. J.*, 246:1–17 (1987); Gerit, J. A., *Chem. Rev.*, 87:1079–1105 (1987)). Alternatively, where a particular sequence alteration is desired, methods of site directed mutagenesis can be employed (Craig, C. S., *Science*, 228:291–297 (1985); Cronin, C. S. et al., *Biochem.*, 27:4572–4579 (1988); Wilks, H. M. et al., *Science*, 242:1541–1544 (1988)).

DNA sequences encoding SDI-1 and antisense SDI-1 DNA sequences can be isolated from the plasmid pSDII (Noda, A., et al., *Exp. Cell Res.*, 211:900–98 (1994)).

An antisense SDI-1 DNA sequence means a DNA sequence which is complementary to the mRNA transcribed from the endogenous SDI-1 gene or a fragment thereof (and which is transcribed into a mRNA which is complementary to the endogenous SDI-1 gene or a fragment thereof), and which is capable of hybridizing with binding to the SDI-1 mRNA or endogenous SDI-1 gene and thereby inhibit the production of SDI-1.

In one embodiment of the invention, the antisense SDI-1 DNA sequence is a sequence which is transcribed into a mRNA which is complementary to the full length endogenous SDI-1 gene.

The antisense SDI-1 DNA sequence can also be a sequence which is transcribed into a mRNA which is complementary to a fragment of the endogenous SDI-1 gene. Such antisense SDI-1 DNA sequences are preferably 15 to 250 nucleotides, or more preferred 10 to 30 nucleotides, and most preferred 15 to 24 nucleotides long and are preferably in accordance with the nucleotide sequence of SDI-1.

Such antisense SDI-1 DNA sequences may be obtained using solid phase oligonucleotide synthetic methods, however, more preferably, such molecules can be obtained via the polymerase-mediated, template-dependent extension of a primer molecule that is antisense to a fragment of an SDI-1 nucleic acid molecule.

According to the present invention a retroviral vector is constructed which carries DNA sequences encoding SDI-1, functional analogues of SDI-1, or fragments thereof, an antisense SDI-1 DNA sequences.

The use of retroviral vectors for gene therapy has received much attention and is currently the method of choice for the transferred of therapeutic genes in a variety of approved protocols both in the USA and in Europe (Kotani, H. et al., *Human Gene Therapy*, 5:19–28 (1994)).

Retroviral vector systems consist of two components:
1) The retroviral vector itself is a modified retrovirus (vector plasmid) in which the genes encoding for the viral proteins (gag, pol, and or env) have been replaced by therapeutic genes and marker genes to be transferred to the target cell. Such a retroviral vector comprises a 5'LTR-region of the structure U3-R-U5; one or more sequences selected from coding and non-coding sequences replacing the gag, pol and/or env coding sequences; and a 3'LTR-region of the structure U3-R-U5. Since the replacement of the genes encoding for the viral proteins effectively cripples the virus it must be rescued by the second component in the system which provides the missing viral proteins to the modified retrovirus.

The second component is:
2) a cell line that produces large quantities of the viral proteins (gag, pol, and/or env), however lacks the ability to produce replication competent virus. This cell line is known as the packaging cell line and consists of a cell line transfected with DNA constructs (e.g. one or more plasmids) carrying the genes encoding the viral proteins enabling the modified retroviral vector to be packaged.

To generate the packaged vector, the retroviral vector is transfected into the packaging cell line. Under these conditions the modified retroviral genomic including the inserted therapeutic and marker genes is transcribed from the retroviral vector and packaged into the modified retroviral particles recombinant viral particles). These recombinant viral particles is then used to infect target cells in which the vector genome and any carried marker or therapeutic genes become integrated into the target cell's DNA. A cell infected with such a recombinant viral particle cannot produce new vector virus since no viral proteins are present in these cells (the virus is replication defective). However the DNA of the vector carrying the therapeutic and marker genes is integrated in the cell's DNA and can now be expressed in the infected cell.

Retroviral vector systems have been optimized to minimize the chance of replication competent virus being present. However it has been well documented that recombination events between components of the retroviral vector system can lead to the generation of potentially pathogenic replication competent virus and a number of generations of vector systems have been constructed to minimize this risk of recombination (Reviewed in Salmons, B., and Günzburg, W. H., *Human Gene Therapy*, 4:129–141 (1993)).

A further consideration when considering the use of in vivo gene therapy, both from a safety stand point and from a purely practiced stand point, is the targeting of retroviral vectors. It is clear that therapeutic genes carried by vectors should not be indiscriminately expressed in all tissues and cells, but rather only in the requisite target cell.

A number of retroviral vector systems have been previously described that should allow targeting of the retroviral vector (Salmons, B., and Günzburg, W. H., *Human Gene Therapy*, 4:129–141 (1993)). Most of these approaches involve either limiting the infection event to predefined cell types or using heterologous promoters to direct expression of linked heterologous therapeutic or marker genes to specific cell types. Heterologous promoters are used which should drive expression of linked genes only in the cell type in which this promoter is normally active. These promoters are inserted, in combination with the marker or therapeutic gene, in the body of the retroviral vectors, in place of the gag, pol or env genes.

Retroviral vectors according to the invention also includes retroviral vectors based on Self Inactivating-Vectors (SIN) in which retroviral promoters are functionally inactivated in the target cell (WO-Al-94 29437). Further modifications of these vectors include the insertion of promoter gene cassettes within the LTR region to create double copy vectors (WO-Al-89 11539). In both of these vectors the heterologous promoters is inserted either in the body of the vector, or in the LTR region, directly linked to the therapeutic gene.

In a preferred embodiment of the invention the retroviral vector used is a retroviral vector of the ProCon type as described in WO 96/07748.

The retroviral genome consists of an RNA molecule with the structure R-U5-gag-pol-env-U3-R. During the process of reverse transcription, the U5 region is duplicated and placed at the right hand end of the generated DNA molecule, whilst the U3 region is duplicated and placed at the left hand end of the generated DNA molecule. The resulting structure U3-R-U5 is called LTR (Long Terminal Repeat) and is thus identical and repeated at both ends of the DNA structure or provirus (Varmus, H., *Science*, 240:1427–1435, (1988)). The U3 region at the left hand end of the provirus harbours the promoter and transcriptional regulatory sequences. This promoter drives the synthesis of an RNA transcript initiating at the boundary between the left hand U3 and R regions and terminating at the boundary between the right hand R and U5 region. This RNA is packaged into retroviral particles and transported into the target cell to be infected. In the target cell the RNA genome is again reverse transcribed as described above.

In the ProCon-vector the right hand U3 region is altered, but the normal left-hand U3 structure is maintained; the vector can be normally transcribed into RNA utilizing the normal retroviral promoter located within the left-hand U3 region. However the generated RNA will only contain the altered right-hand U3 structure. In the infected target cell, after reverse transcription, this altered U3 structure will be placed at both ends of the retroviral structure. If the altered region carries a polylinker (see below) instead of the U3 region then any promoter, including those directing tissue specific expression such as the WAP promoter can be easily inserted. This promoter will then be utilized exclusively in the target cell for expression of linked genes carried by the retroviral vector. Additionally DNA segments homologous to one or more cellular sequences can be inserted into the polylinker for the purposes of gene targeting, by homologous recombination.

Other means of directing gene expression to target tissue is to use target cell specific regulatory elements or promoters. The target cell specific regulatory elements and promoters are selected from one or more elements of the group consisting of Whey Acidic Protein (WAP). Mouse Mammary Tumour Virus (MMTV), β- lactoglobulin and casein specific regulatory elements and promoters, pancreas specific regulatory elements and promoters including carbonic anhydrase II and β-glucokinase regulatory elements and promoters, lymphocyte specific regulatory elements and promoters including immunoglobulin and MMTV lymphocytic specific regulatory elements and promoters and MMTV specific regulatory elements and promoters conferring responsiveness to glucocorticoid hormones or directing expression to the mammary gland.

The LTR regions are selected from at least one element of the group consisting of LTRs of Murine Leukaemia Virus (MLV), Mouse Mammary Tumour Virus (MMTV), Murine Sarcoma Virus (MSV), Simian Immunodeficiency Virus (SIV), Human Immunodeficiency Virus (HIV), Human T-cell Leukacmia Virus (HTLV), Feline Immunodeficiency Virus (FIV), Feline Leukaemia Virus (FeLV), Bovine Leukaemia Virus (BLV) and Mason-PfizerMonkey virus (MPMV).

In a preferred embodiment, the retroviral vector according to the invention comprises a DNA encoding SDI-1, a functional analogue, or a fragment thereof, or antisense SDI-1 DNA sequence under transcriptioal control of human mammary specific regulatory elements, such as the WAP or MMTV regulatory sequences. Such retroviral vectors are useful for delivering the antiproliferative activity of SDI-1 to human mammary carcinoma cells, and will therefore be useful for the treatment of human mammary carcinoma. A great advantage of these retroviral vectors is that the retroviral particles can be spread in the blood stream similarly to metastazing tumour cells, which will make it possible to eliminate micrometastazes long before they can be detected by conventional methods.

The WAP regulatory element can be isolated from pWP2-HGH (Günzburg, W. H., *Molecular Endocrinology*, 5: 123–133, (1991)). In a preferred embodiment the WAP regulatory element contains the 320 bp XhoI XbaI fragment of the WAP promoter region, and in a particularly preferred embodiment, the WAP regulatory element is the proximal 445 bp of the WAP promoter.

The MMTV U3-region can be isolated from the plasmid pBG102. In a particular, preferred embodiment the MMTV regulatory element comprises the U3 region of MMTV without the inverted repeats. Fragments of the MMTV promoter containing the 0.6 Kb PstI MMTV promoter fragment can also be used.

In another embodiment of the invention the retroviral vector according to the invention carries the DNA encoding SDI-1, a functional analogue, or a fragment thereof, or antisenses SDI-1 DNA sequence under transcriptional control of X-ray inducible promoters, such as those from the tissue plasminogen activator and EGR1 genes (for an overview see Fornace, *Ann. Rev. Genet.*, 26:507–526 (1992)).

The retroviral vector according to the invention can also carry a marker gene.

The marker carried by the viral vector can be, for example, genes which code for proteins such as β-galactosidase, neomycin, alcohol dehydrogenase, luciferase, puromycin, hypoxanthine pohsphoribosyl transferase (HPRT), hygromycin, secreted alkaline phosphatase and green or blue fluorescent proteins.

The retroviral vectors of the invention are based preferably either on a BAG vector (Price, J. D. Turner, and C. Cepko, *Proc. Natl. Acad. Sci USa*, 84:156–160 1987) or an LXSN vector (Miller, A. D. and G. J. Rossman, *Biotechniques*, 7:980–990 (1989)).

The packaging cell line can be selected from an element of the group consisting of psi-2 (Mann, R., et al., *Cell*, 33:153–159 (1983)), psi-Crip (Danos, O. and Mulligan R. C., *Proc. Natl. Acad. Sci. USA*, 85:6460–6464 (1988)), psi-AM (Cone, R. D. and Mulligan, R. C., *Proc. Natl. Acad. Sci. USA*, 81:6349–6353 (1984)). GP-E-86 (Markowitz, D., et al., *J. Virol.*, 62:1120–1124 (1988a)). PA317 (Miller, A. D. and Buttimore, C., *Mol. Cell. Biol.*, 6:2895–2902 (1986)). GP+envAM-12 (Markowitz, D., et al., *Virology*, 167:400–406 (1988b)). Bose 23, Bing (Pear, W. S. et al., *Proc. Natl. Acad. Sci. USA*, 90:8392–8396 (1993)) or FLYA1 3, FLYRD18 (Cosset, F. L., et al., *J. Virol.* 69:74309–7436 (1995)) or of any of these transfected with recombinant constructs allowing expression of surface proteins from other enveloped viruses. Such pseudotyped retroviral particles are described in PCT/EP96/01348.

In a particular preferred embodiment, the packaging cell line is made from human cells, e.g., HT1080 cells (WO-Al-9621014), or 293 (Graham et al., *J. Gen. Viol.* 36:59 1977)) thereby allowing production of recombinant retroviruses that are capable of surviving inactivation by human serum.

Another embodiment of the invention envisages the alteration or partial deletion of at least one retroviral sequence required for the integration of the retrovirus.

According to the invention the term "polylinker" is used for a short stretch of artificially synthesized DNA which carries a number of unique restriction sites allowing the easy insertion of any promoter or DNA segment.

The term "heterologous" is used for any combination of DNA sequences that a not normally found intimately associated in nature.

Preservation and administration of Retroviral particles

Recombinant retrovirus which has been purified or concentrated may be preserved by first adding a sufficient amount of a formulation buffer to the media containing the recombinant retrovirus, in order to form an aqueous suspension. The formulation buffer is an aqueous solution that contains a saccharide, a high molecular weight structural additive, and a buffering component in water. The aqueous solution may also contain one or more amino acids.

The recombinant retrovirus can also be preserved in a purified form. More specifically, prior to the addition of the formulation buffer, the crude recombinant retrovirus described above may be clarified by passing it through a filter, and then concentrated, such as by a cross flow concentrating system (Filtron Technology Corp., Northborough, Mass.). Within one embodiment, DNase is added to the concentrate to digest exogenous DNA. The digest is then diafiltrated to remove excess media components and establish the recombinant retrovirus in a more desirable buffered solution. The diafiltrate is then passed over a Sephadex S-500 gel column and a purified recombinant retrovirus as eluted. A sufficient amount of formulation buffer is added to this eluate to reach a desired final concentration of the constituents and to minimally dilute the recombinant retrovirus, and the aqueous suspension is then stored, preferably at −70° C. or immediately dried. As noted above, the formulation buffer is an aqueous solution that contains a saccharide, a high molecular weight structured additive, and a buffering component in water. The aqueous solution may also contain one or more amino acids.

The crude recombinant retrovirus can also be purified by ion exchange column chromatography. In general, the crude recombinant retrovirus is clarified by passing it through a filter, and the filtrate loaded onto a column containing a highly sulfonated cellulose matrix. The recombinant retorvirus is eluted from the column in purified form by using a high salt buffer. The high salt buffer is then exchanged for a more desirable buffer by passing the eluate over a molecular exclusion column. A sufficient amount of formulation buffer is then added, as discussed above, to the purified recombinant retrovirus and the aqueous suspension is either dried immediately or stored, preferably at −70° C.

The aqueous suspension in crude or purified form can be dried by lyophilisation or evaporation at ambient temperature. Specifically, lyophilisation involves the steps of cooling the aqueous suspension below the glass transition temperature or below the eutectic point temperature of the aqueous suspension, and removing water from the cooled suspension by sublimation to form a lyophilised retrovirus. Once lyophilised, the recombinant retrovirus is stable and may be stored at −20° C. to 25° C., as discussed in more detail below.

Within the evaporative method, water is removed from the aqueous suspension at ambient temperature by evaporation. Water can also be removed through spray drying.

The aqueous solutions used for formulation, as previously described, are composed of a saccharide, high molecular weight structural additive, a buffering component, and water. The solution may also include one or more amino acids. The combination of these components act to preserve the activity of the recombinant retroviruses upon freezing and lyophilization, or drying through evaporation.

The high molecular weight structural additive aids in preventing viral aggregation during freezing and provides structural support in the lyophilised or dried state. Within he context of the present invention, structural additives are considered to be of "high molecular weight" if they are greater than 5000 m.w. A preferred high molecular weight structural additive is human serum albumin.

The amino acids, if present, function to further preserve viral infectivity upon cooling and thawing of the aqueous suspension. In addition, amino acids function to further prevent viral infectivity during sublimation of the cooled aqueous suspension and while in the lyophilised state.

The buffering component acts to buffer the solution by maintaining a relatively constant pH. A variety of buffers may be used, depending on the pH range desired, preferably between 7.0 and 7.8.

Aqueous solutions for the formulation of recombinant retroviruses are described in detail in WO-A2-96121014.

In addition, it is preferable that the aqueous solution contain a neutral salt which is used to adjust the final formulated recombinant retrovirus to an appropriate iso-osmotic salt concentration.

Lyophilized or dehydrated retroviruses may be reconstituted using a variety of substances, but are preferably reconstituted using water. In certain instances, dilute salt solutions which bring the final formulation to isotonicity may also be used. In addition, it may be advantageous to use aqueous solutions containing components known to enhance the activity of the reconstituted retrovirus. Such components include cytokines, such as IL-2, polycations, such as prolamine sulfate, or other components which enhance the transduction efficiency of the reconstituted retrovirus. Lyophilized or dehydrated recombinant retrovirus may be reconstituted with any convenient volume of water or the reconstituting agents that allow substantial, and preferably total stabilization of the lyophilized or dehydrated sample.

Recombinant retroviral particles may be administered to a wide variety of locations including, for example, into sites such as an organ or to the site of a tumor. Within other embodiments, the recombinant retrovirus may be administered orally, intravenously, buccal/sublingual, intraperitoneally, or subcutaneously. The daily dosage depends upon the exact mode of administration, form in which administered, the indication toward which the administration is directed, the subject involved and the body weight of the subject involved, and further the preference and experience of the physician in charge.

The routes of administration described herein may be accomplished simply by direct administration using a needle, catheter or related device. In particular, within certain embodiments of the invention, one or more dosages may be administered directly.

In another embodiment of the invention a cell line producing retroviral particles according to the invention, is encapsulated in a porous membrane which is permeable to the viral particles produced (Stange, J., et al., *Biomat. Art. Cells & Immob. Biotech.* 27:343–352 (1993) and UK patent application 2 135 954)).

Upon implantation, vector virus is released but the capsule material protects the virus producing cells from the immune system.

The encapsulated cells according to the invention can be prepared for example by suspending the cells in an aqueous solution of a polyelectrolyte (e.g. selected from sulphate group-containing polysaccharides or polysaccharide derivatives or of sulphonate group containing synthetic polymers), whereafter the suspension in the form of preformed particles is introduced into a precipitation bath containing an aqueous solution of a counter-charged polyelectrolyte (such as for example a polymer with quaternary ammonium groups).

Sulphate group-containing polysaccharides or polysaccharide derivatives includes cellulose sulphate, cellulose acetate sulphate, carboxymethylcellulose sulphate, dextran sulphate or starch sulphate in the form of a salt, especially a sodium salt. The sulphonate group-containing synthetic polymer can be a polystyrene sulphonate salt, preferably a sodium salt.

Polymers with quaternary ammonium groups includes polydimethyldiallylammonium or polyvinylbenzyl-trimethylammonium, in the form of a salt thereof, preferably a chloride salt.

Such capsules are preferably prepared by suspending the cells of the invention in a solution containing 0.5–50%, preferably 2–5%, sodium cellulose sulphate and 5% fetal calf serum in buffered saline. This suspension is then dropped by a dispensing system (e.g., air-jet system or piezoelectric system) while stirring into a precipitation bath containing 0.5%–50%, preferably 2–10%, or most preferred 3% polydimethyl-diallylammonium chloride in buffered saline. Capsule formation occurs within milliseconds and the capsules containing cells are kept in the precipitation bath for 30 seconds to 5 minutes and then washed. The rapidity of this method ensures that the cells are not unduly stressed during the whole procedure (Stange, J., et al., *Biomat. Art. Cells & Immuob. Biotech.* 21:343–352 (1993)).

The encapsulated cells can be cultivated in a normal cell culture medium (the nature of which depends on the encapsulated cells) at standard conditions of humidity, temperature and $CO_2$ concentration. During this culture period, production of viral particles from the capsules into the cell culture medium can be demonstrated using RT-PCR technology or by transfer of cell free (0.45 mm filtered) supernatant to target cells followed by the demonstration of viral infection by assay for the activity of marker proteins encoded by genes carried by the viral vector construct contained within the viral particle. If the marker gene carried by the viral vector is a gene conferring resistance to a specific compound upon the target cell of the product of which is easily assayed on a cell to cell basis (e.g., green or blue fluorescent protein), the titre of virus produced by the system can be ascertained.

After a suitable period in culture (normally not less than 1 hour and not exceeding 30 days), the cell containing capsules can be surgically implanted either directly, or by injection using a syringe into various areas of the body including the breast.

The recombinant DNA methods employed in practicing the present invention are standard procedures, well known to those skilled in the art, and described in detail, for example, "Molecular Cloning" (Sambrook, J., E. F. Fritsch and T. Maniatis, 1989, Molecular Cloning, Cold Spring Harbor Laboratory Press, New York, USA) and in "A Practical Guide to Molecular Cloning" (Perbal, B. 1984. A Practical Guide to Molecular Cloning, John Wiley & Sons.).

The following examples will illustrate the invention further. The examples are however in no way intended to limit the scope of the present invention as obvious modifications will be apparent, and still other modifications and substitutions will be apparent to anyone skilled in the art.

EXAMPLE 1

Deletion of the U3 Region and Insertion of a Polylinker

In the numeric leukemia virus (MLV) retroviral vector known as BAG the β-galactosidase gene is driven by the promiscuous (i.e. non-tissue specific) MLV promoter in the U3 region of the LTR. According to the present invention a derivative of the BAG vector has been constructed in which the MLV promoter (U3) located within the 3'LTR except the inverted repeat has been deleted by PCR and replaced by a polylinker. The BAG vector lacking the U3 is expressed from the MLV promoter (U3) within the 5'LTR when introduced into a package cell line. As a result of the rearrangements occurring in the retroviral genome during its life cycle, following infection of its target cell, the polylinker will be duplicated at both ends of the retroviral genome as described in WO-A1-9607748. Thereby a retroviral vector can be constructed in which the expression of the β-galactosidase gene of BAG will be controlled by any heterologous promoter inserted into the polylinker. As a template for PCR we used pBAGN a plasmid carrying a derivative of the BAG construct carrying only one LTR, created by NheI digest of the original pBAG (Price, J., et al., *Proc. Natl. Acad. Sci. U.S.A.* 84:156–160 (1987)) followed by a self-ligation of the 7018 bp fragment.

Figure 2A:
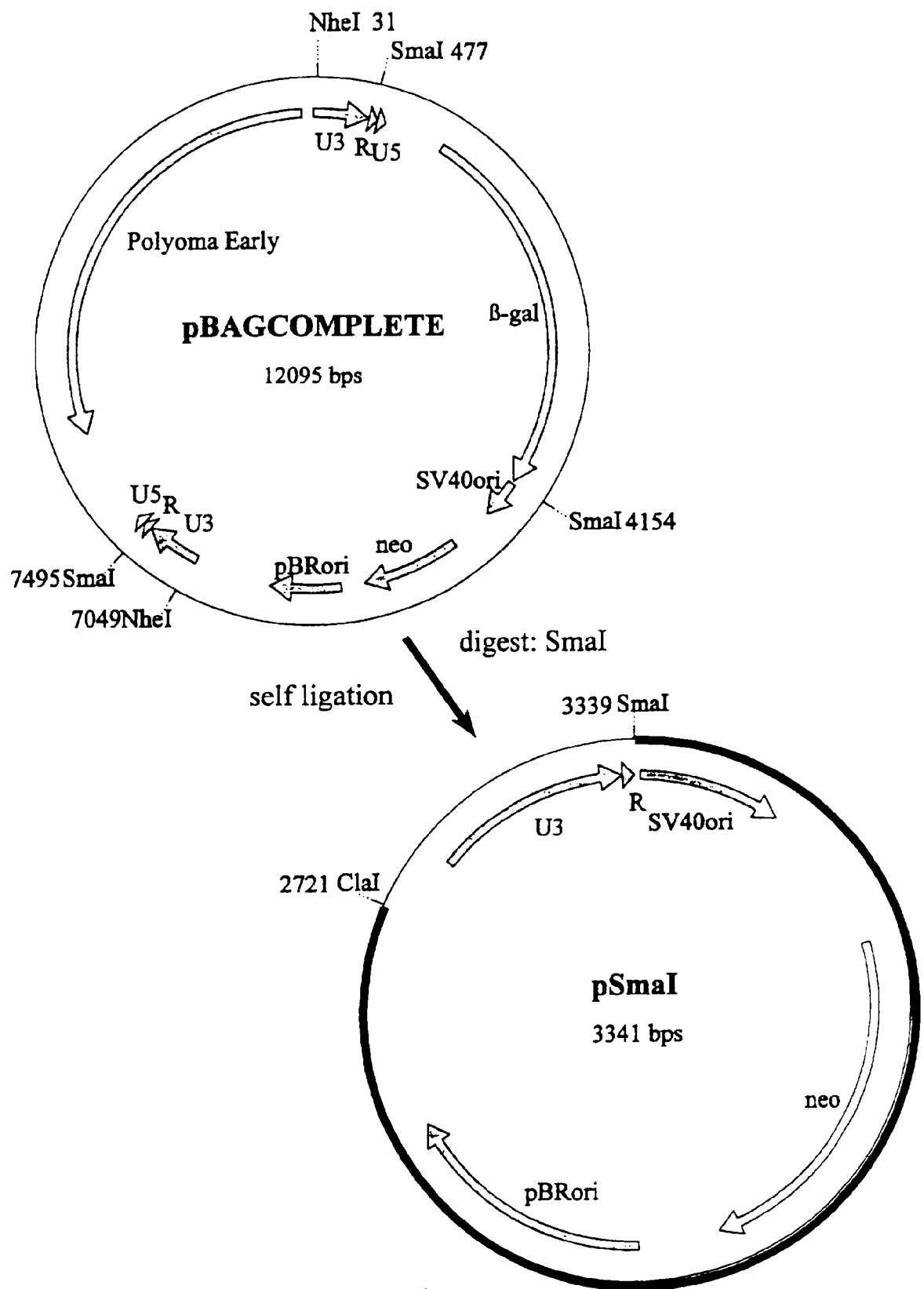
FIGS. 2A–2B: Construction of plasmid pSmaU3del.
Figure 2B:
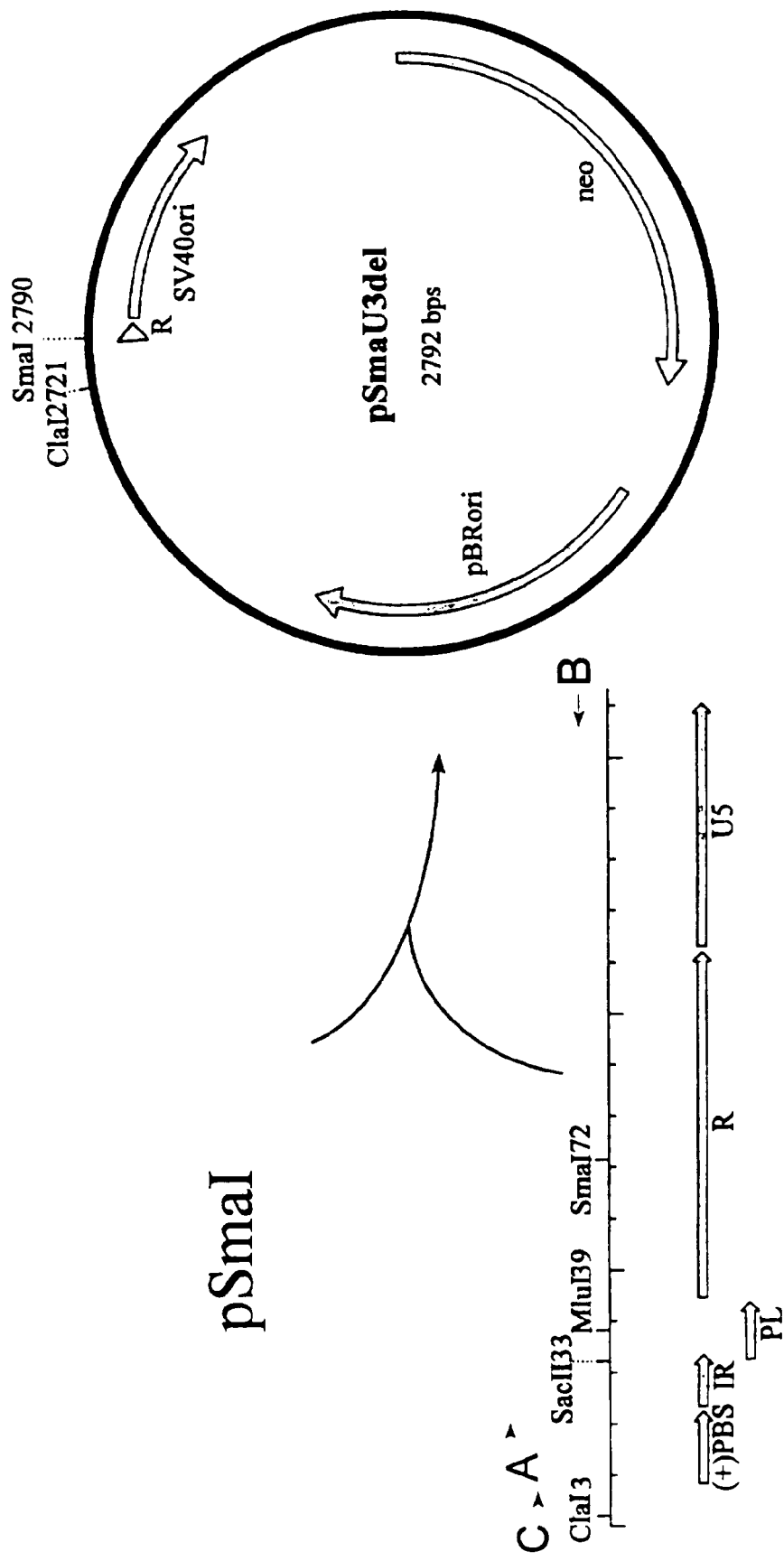

The 3' end of primer A is complementary to the R-region of the LTR (FIG. 1). The 5' extension contains an artificial (art.) polylinker and an artificial inverted repeat (IR(art)). Primer β is complementary to the U5 region of the LTR (FIG. 1). After 35 cycles of annealing at 47° C. and extension at 60° C. at 140 bp product was obtained, which was used as a template for the second PCR. In this reaction a Cla-I site and an artificial (+)PBS was added 5' of the IR-region using primer C (FIG. 1) in combination with primer B. Annealing was carried out at 53° C. and extension at 72° C. After 35 cycles to 163 bp product was obtained, which was digested with ClaI and SmaI and ligated to a 2722 bp (ClaI/SmaI fragment of pSmaI (a derivative of pBAG (=pBAG complete) prepared by digestion with SmaI followed by a Self ligation of the 3341 bp fragment) (FIGS. 2A–2B). The resulting plasmid pSmaU3del (2792 bp) was linearized by a SmaI digest and ligated to the 3677 bp SmaI fragment of pBAGN (FIGS. 3A–3B) to give the plasmid pBAGNU3del (6469 bp). Deletion of the U3 region was confirmed by sequencing from the ClaI-site into the U5-region using pSmaU3del as a template.

Figure 3A:
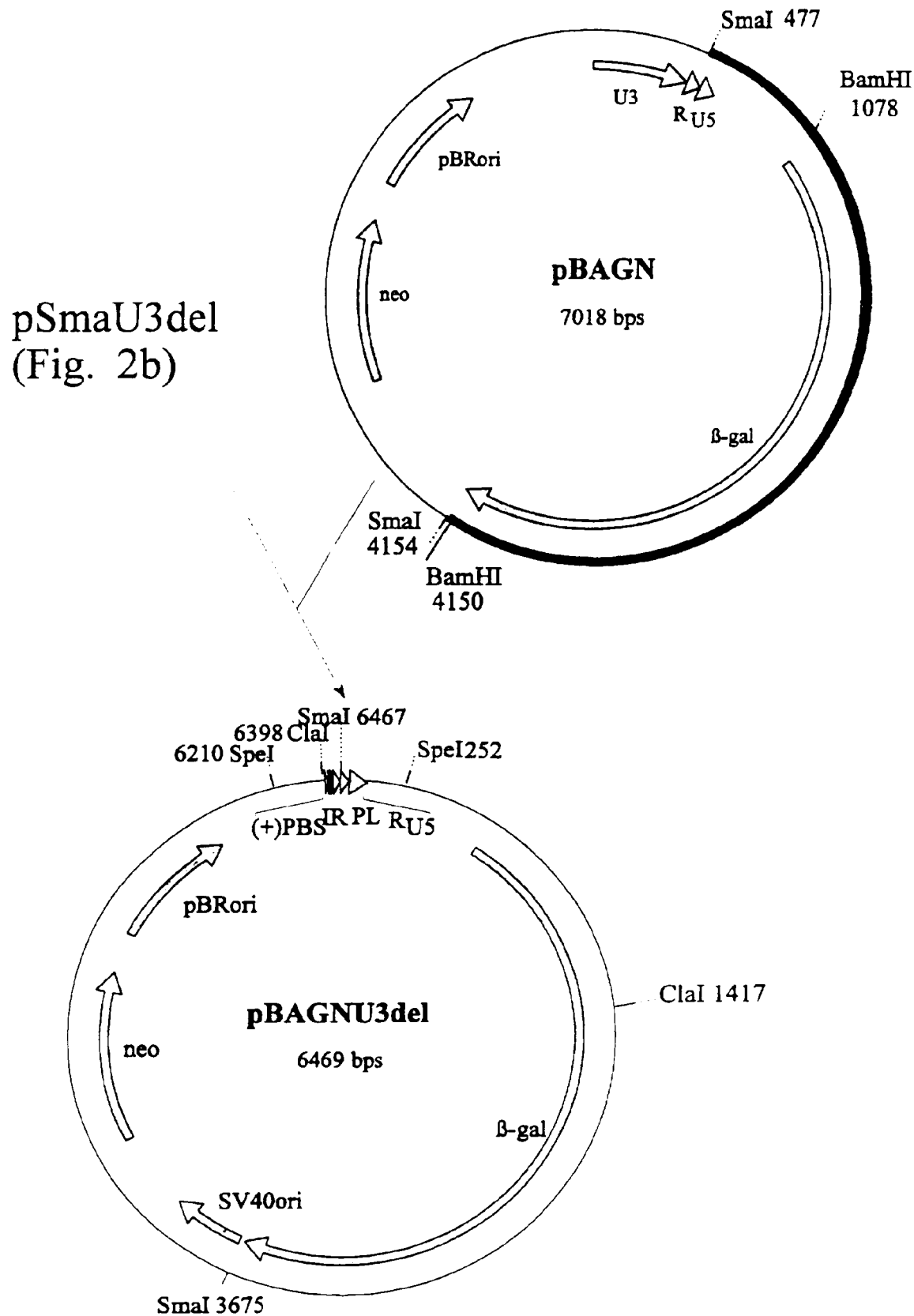
FIGS. 3A–3B: Construction of plasmids pBAGNU3del and pCON6.
Figure 3B:
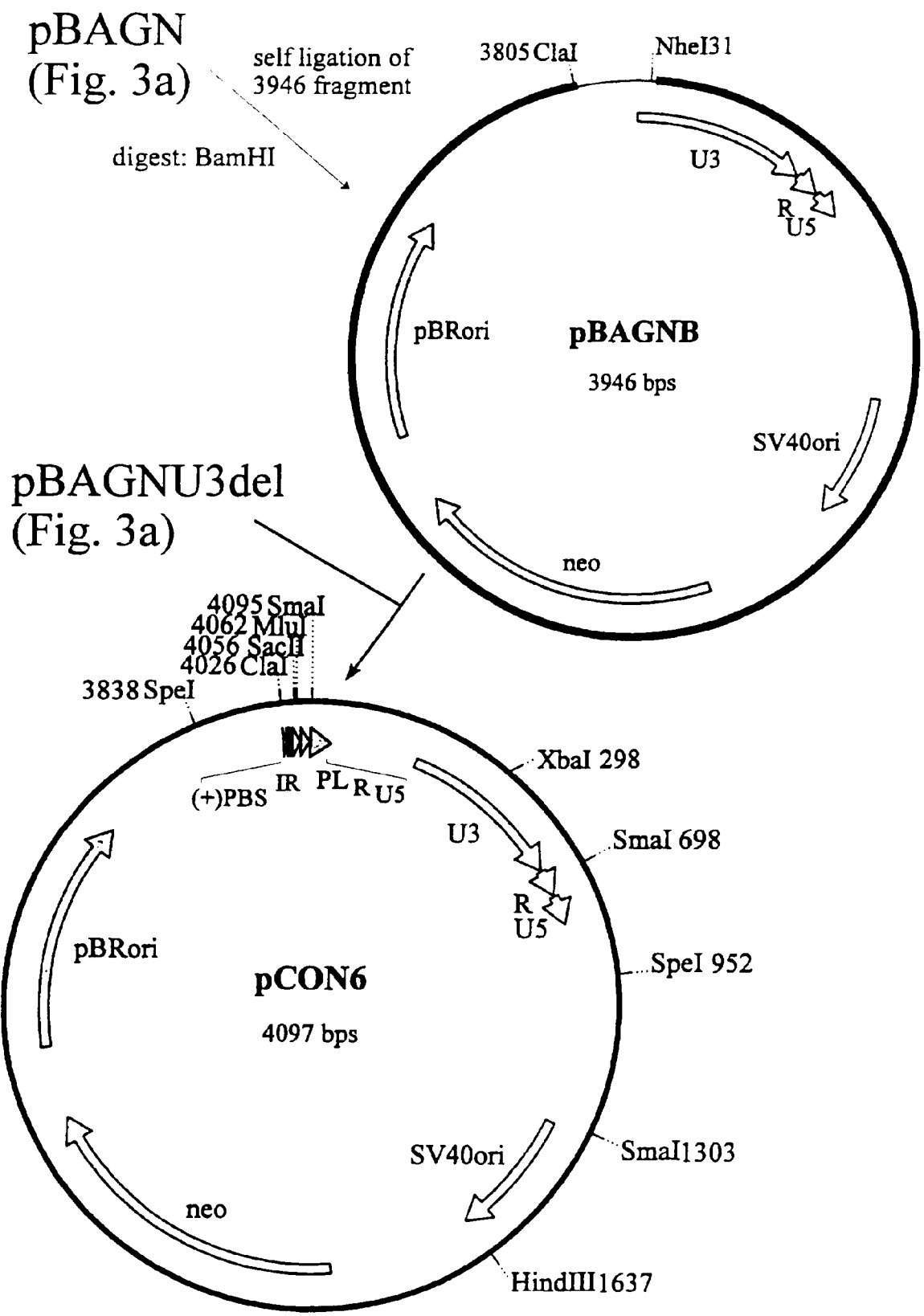

A ClaI SpeI (322 bp) fragment containing the U3 deleted LTR was ligated to a ClaI NheI fragment of pBAGNB (created by self ligation b a 3946 bp BamHI fragment of pBAGN) to give the plasmid of pCON6 (4069 bp) (FIGS. 3A–3B). This plasmid carrying a full U3-minus retroviral vector was used as a basis for further cloning using the inserted polylinker containing the restriction sites SacI and MluI.

According to the principle set forth above the MMTV U3-region has been inserted into the polylinker region or the modified BAG vector.

EXAMPLE 2

Cloning of pMMTV Gal the Mouse Mammary Tumour Virus (MMTV) U3-Region (mtv-2) without the inverted repeats including a region that confers responsiveness to glucocorticoid hormones and a region containing an element that directs expression to the mammary gland was inserted into pCON6.

Figure 5:
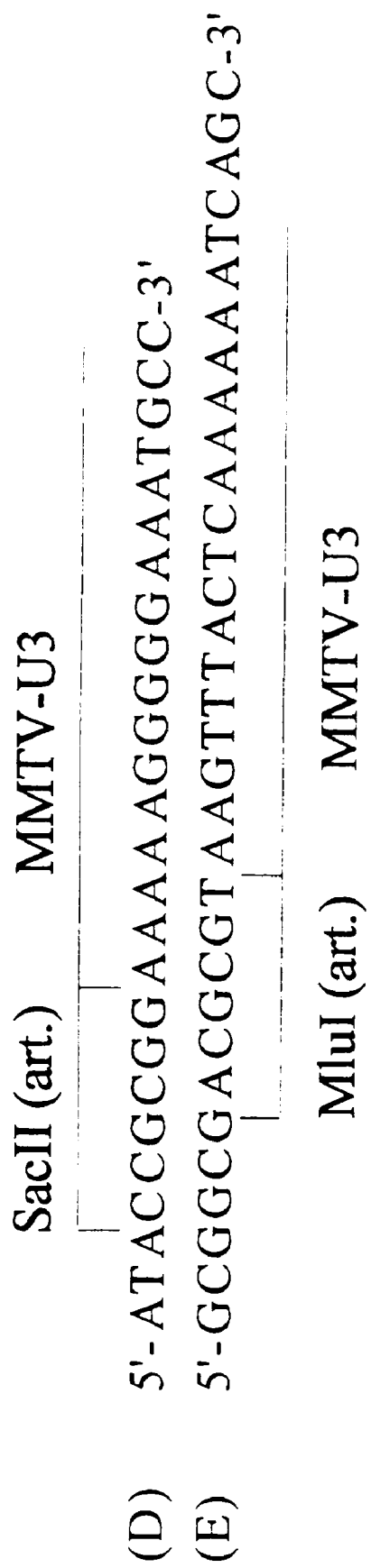
FIG. 5: Primers D (SEQ ID NO: 4) and E (SEQ ID NO: 5) used for amplification of the U3-region of MMTV.

The U3 region of MMTV was amplified by PCR using the plasmid pBG102 (a plasmid containing the 3'LTR from mtv 2) as a template with primers D and E. The 3' end of primer D is complementary to the 5' end of the MMTV U3 region and carries a SacI site in its 5' extension (FIG. 5). The 3' end of primer E is complementary to the 3' end of the MMTV U3 region and has a MluI site in its 5'0 extension (FIG. 5).

Figure 4A:
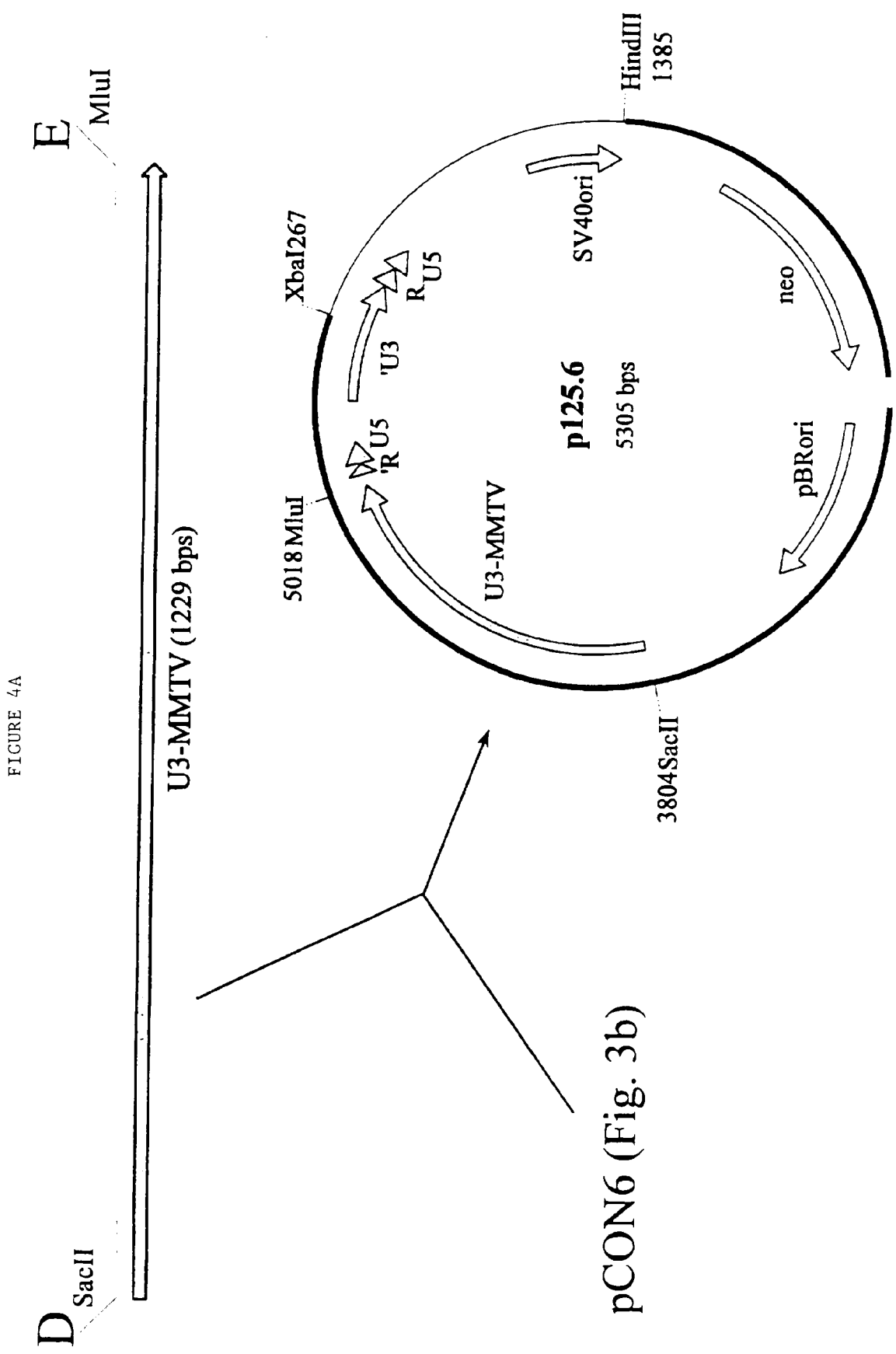
FIGS. 4A–4B: Construction of plasmid pMMTV-BAG.
Figure 4B:
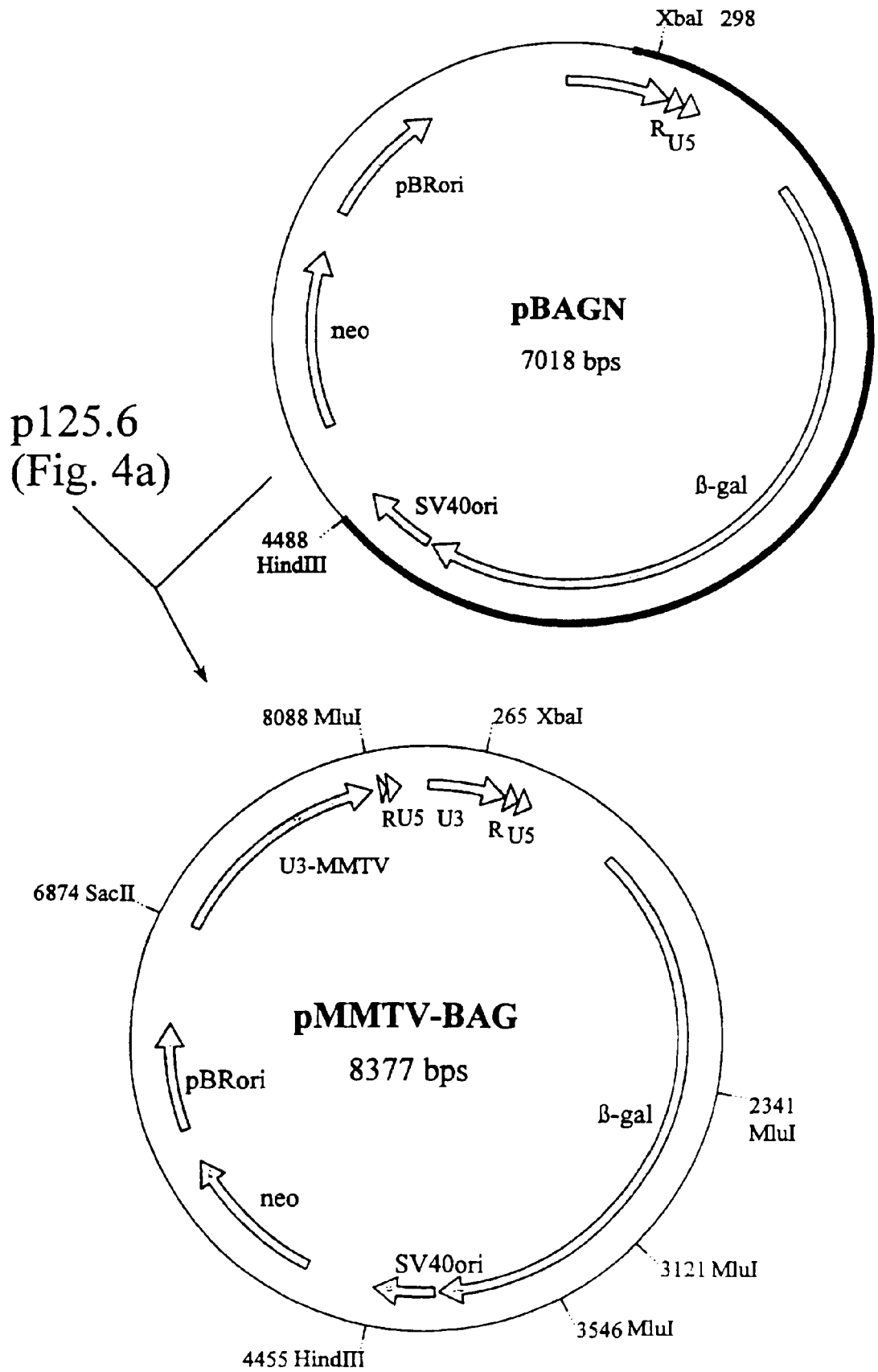
Figure 6:
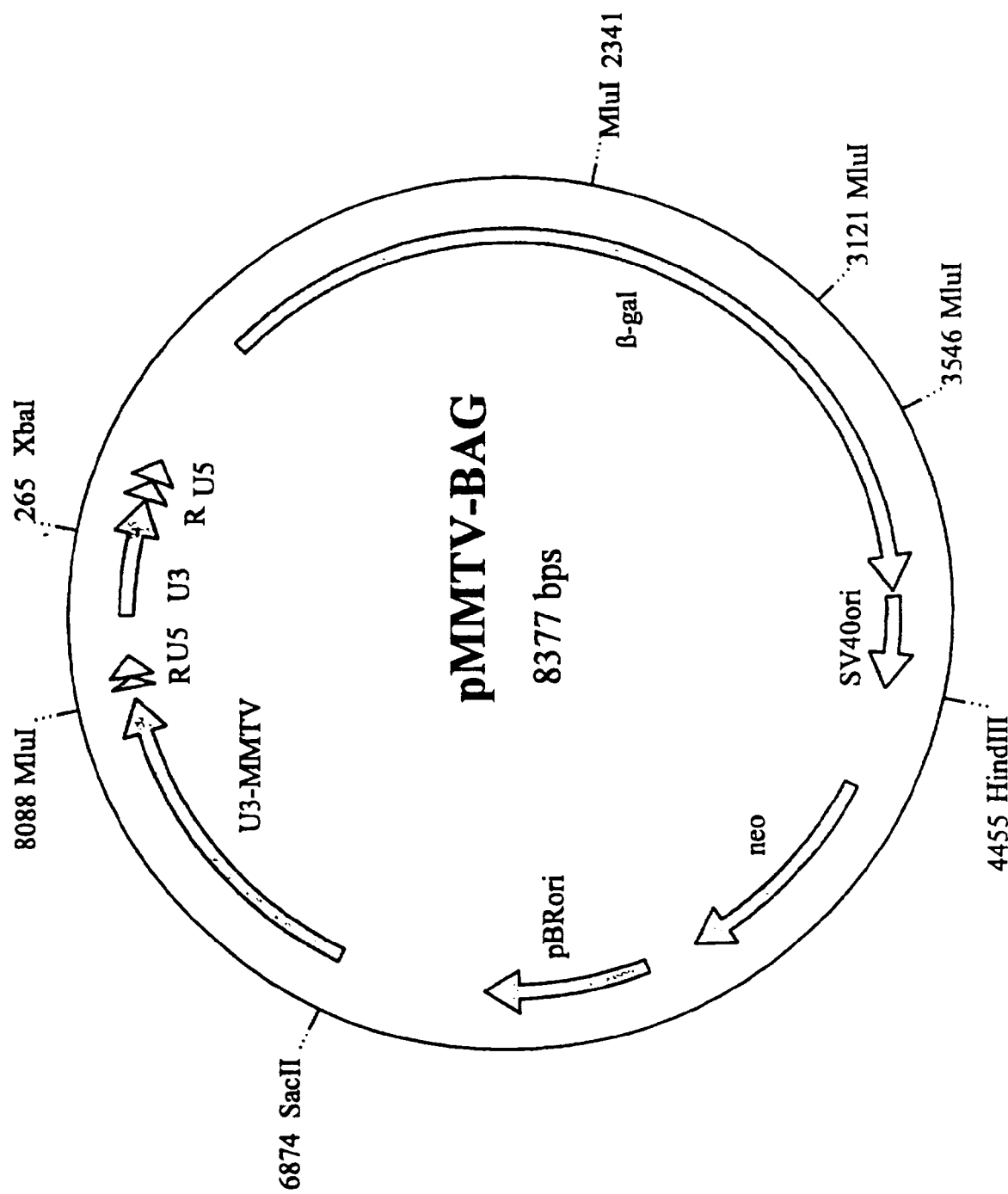
FIG. 6: Plasmid pMMTV-BAG.

After 35 cycles of annealing at 49° C. and extension at 72° C., a 1229 bp product was obtained, digested with SacI and MluI and ligated to the SacI/MluI digested vector pCON6. The resulting plasmid p125.6 (5305 bp) (FIGS. 4A–4B) was digested with XhaI and HindIII and the 4187 bp fragment ligated to the XhaI/HindIII 4190 bp fragment of pBAGN containing the β-galactosidase gene to give the plasmid pMMTV-BAG (8377 bp) (FIGS. 4A–4B) in which the β-galactosidase gene is under transcriptional control of the MLN promoter after transfection, and under the MMTV promoter after infection (FIG. 6).

EXAMPLE 3

Construction of ProCon SDI Retroviral Vector

Figure 7:
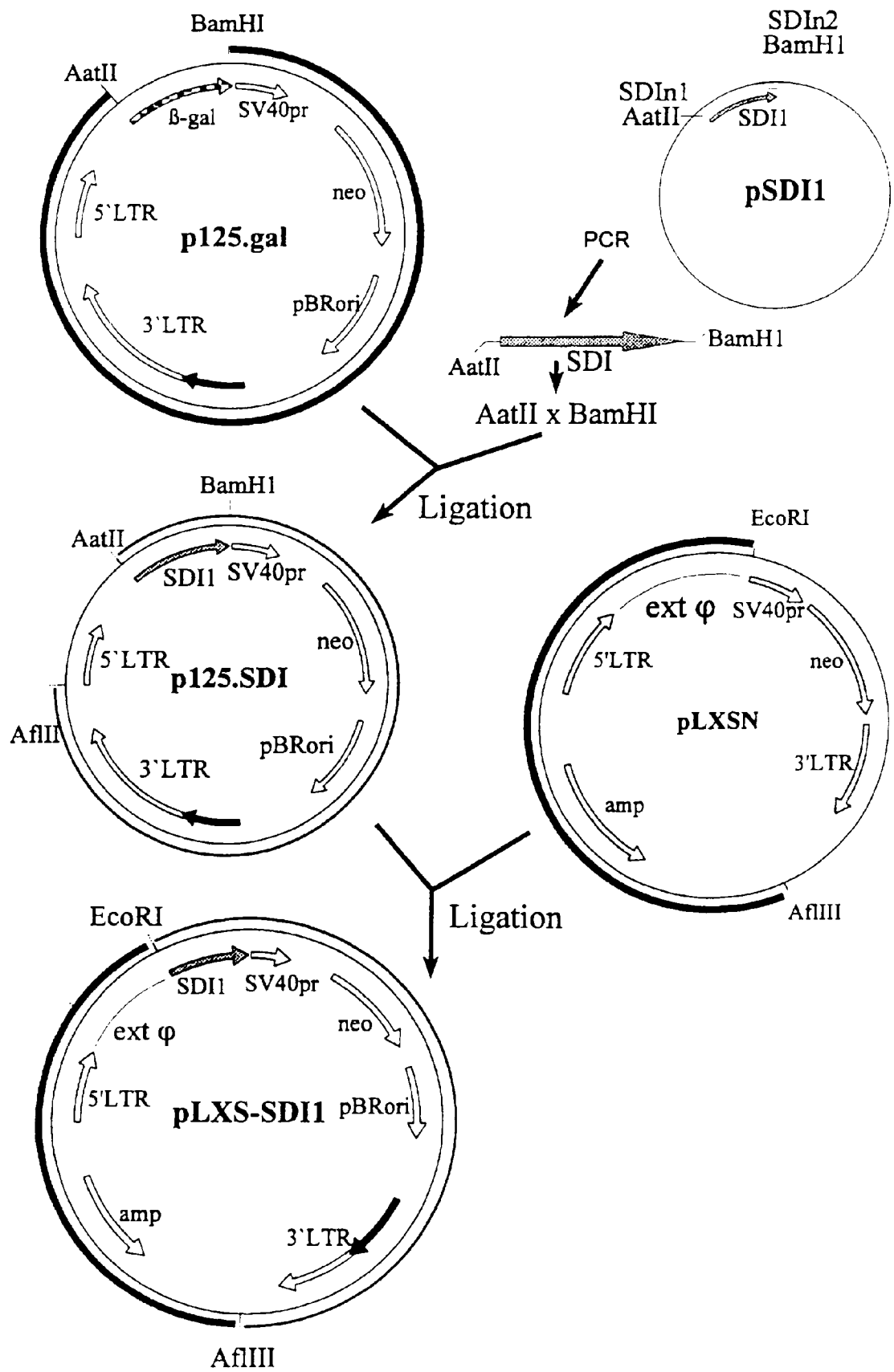
FIG. 7: Retroviral vector cloning strategy for pLXS-SDI-1.

The human SDI-1 CDNA carried in the plasmid PSDII (Noda, A., et al., *Exp. Cell. Res.*, 211:90–98 (1994)) was isolated by PCR using two primers. SDln1:5'-TATG-GACGTCTCCCTGCCGAAGTCAGTT-3' (SEQ ID NO:6) and SDln2: 5'-TATGGGATCCGGCAGAAGATGTA-GAGCG-3' (SEQ ID NO:7), carrying BamHI and AatII restriction sites (bold sequences) as extensions. The plasmid pMMTVBAG was digested with datII and BamHI (FIG. 7). The resulting 5 kb vector containing fragment was ligated to the SDI fragment, creating the plasmid p125.SD1 (FIG. 7). In order to extend the retroviral packaging signal, p125.SDI was digested with AatII and AflII and the resulting 4.9 kb fragment was blunt ended and ligated to a 3.5 kb blunt ended EcoRI/4AflIII fragment of pLXSN (Miller, A. D., & Rosman, G. J., *Biotechniques*, 7:980–990 (1989)), giving the plasmid pLXS-SDH (FIG. 7).

EXAMPLE 4

Transfections and Infections

Cell Culture and Growth Assay:

The human bladder carcinoma derived cell line EJ (Parada, L. F., et al., *Nature*, 297:474–478 (1982)), cat kidney derived CRFK (Crandell, R. A., In vitro, 9:176–185 (1973)) and PA317 retrovirus packaging cells (Miller, A. D. & Buttimore, C., *Mol. Cell. Biol.*, 6:2895–2902 (1986)) were cultured in Dulbecco's modified Eagle's medium (DMEM) containing 10% fetal calf serum (FCS).

For growth studies 5,000 EJ or CRFK cells were plated in each well of a six well plate (Falcon) in DMEM containing 10% FCS either with or without $10^{-6}$M dexamethasone. After 7 days the cells were fixed in methanol:acetic acid (3:1) and stained with Giemsa (Fisher So-G-28).

Transfection:

PA317 packaging cells were seeded in a 10 cm tissue culture dish at a density of $2 \times 10^6$ cells one day prior to lipofection and then lipofected with 4 mg of plasmid pLXS-SDI1 and 2 mg of pHCMV-G (Burns, J. C., et al., *Proc. Natl. Acad. Sci. USA*, 90:8033–8037 (1993)) using the lipofectamine kit from GIBCO BRL according to the manufacturer's instructions. The cells were diluted 1:10 24 hours after transfection and cultured in the usual medium containing additionally 400 mg ml G418 (GIBCO BRL). After 14 days colonies of G418 resistant cell clones were pooled to give a population of retroviral vector producing cells (125 SDI PA317).

Infection:

Infections were performed essentially as described previously (Hornsby, P. J. & Salmons B., *Protocols in cell and tissue culture Module* 26D:2, D:2.1–2.5 (1995)). Briefly, 24 hour conditioned cell culture medium having $2 \times 10^6$ 125SDI/PA317 cells was passed through 0.45 m Millipore filters, polybrene added to a final concentration of 8 mg/ml and 2 ml used to infect $1 \times 10^6$ EJ cells in a 10 cm culture dish. After 4 hrs incubation, 6 ml of cell culture medium (DMEM+10% FCS) was added and the cells cultured overnight. The cells were then trypsinised and one fifth of the total amount of cells were seeded in a new culture dish. After 24 hrs, the cell culture medium was changed to DMEDM+10% FCS containing 800 mg/ml G418 and 14 days later resistant cell clones were isolated.

The ability of dexamethasone to turn on SDI-1 expression and the resulting growth inhibition has been examined in various ways.

EXAMPLE 5

Fluoroscence activated cell scanning of infected cell clones was also performed to determine the proportion of cells in various stages of the cell cycle.

Fluorescent activated cell scanning: $5 \times 10^6$ EJ cells were seeded into T-225 flasks and cultured in DMEM containing 3% FCS with or without $10^6$ M dexamethansone. For serum starvation experiments, cells were kept in DMEM lacking FCS for 24 hrs before medium was changed to 3% FCS. To avoid growth inhibition due to cell-to-cell contact, cells were grown until they reached 40–50% confluence. For cell cycle analysis the DNA was stained according to the micronuclei method (Nusse, M., et al., *Methods in Cell Biology*, 42:149 (1994)). In brief, cells were trypsinized and washed once with phosphate buffered saline. $10^6$ cells were resuspended in 1 ml of Solution 1 (10 mM NaCl, 3.4 mM Na-citrate, 10 mg/ml RNase A. 0.3% Nonidet P-40 and 25 mg/ml ethidium bromide (EB)). After 60 min. incubation a room temperature, 1 ml of Solution 2 (0.07 mM citric acid, 0.25 M sucrose and 40 mg/ml EB) was added. The FACS analyses were performed with a FACSCalibur (Becton Dickinson; excitation of EB with an argon laser, 488 nm: EB fluorescence was detected with a long pass filter (LP 640)). A first grade was set to exclude unspecific debris from nucleic according to side scatter and forward scatter. A gate in Fluorescence 2 width-Fluorescence 2 area dot plot was used to exclude doublers. The DNA content was estimated using a Fluorescence 2 area histogram. Cell cycle distribution was analyzed using the MOD FIT LT program (Verify software house Inc.).

The results from this experiment are presented in the following Table:

| Cell Cycle Phase | (Cell Populations (% of total Cells) | | | |
|---|---|---|---|---|
| | Control | Control + D | SDI | SDI + D |
| $G_1/G_0$ | 45.4 | 52.4 | 50.6 | 61 |
| S | 40.5 | 35.4 | 35.7 | 27 |
| G2/M | 14.1 | 12.2 | 13.7 | 12 |

Figure 8:
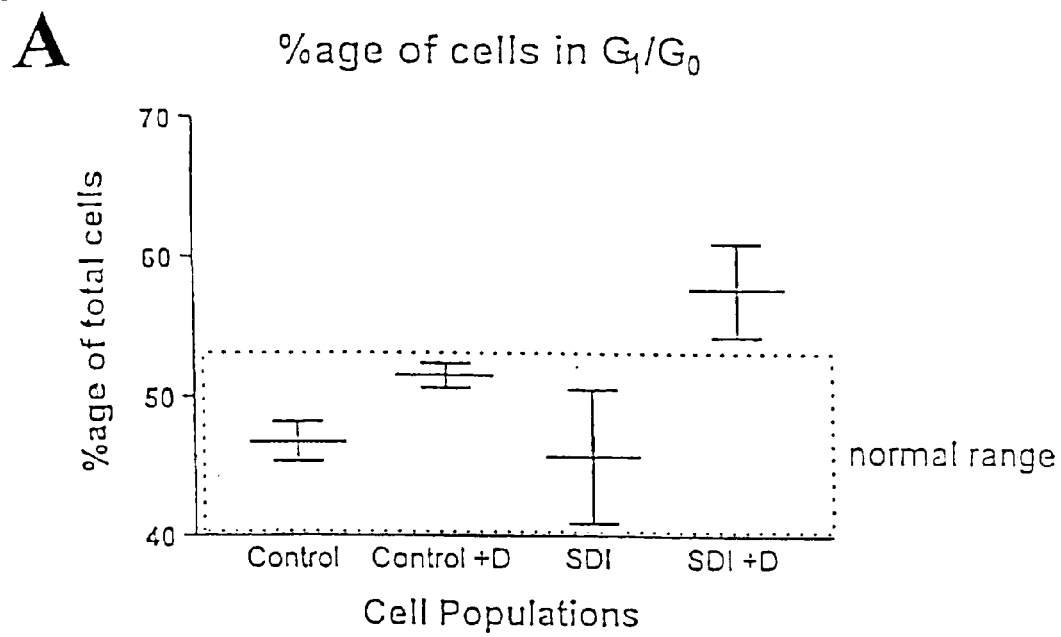
FIGS. 8A–8B: FACS analyzes for cell cycle distribution: the percentage of cells in $G_1/G_0$ phase (FIG. 8A) and S phase (FIG. 8B).
Figure 8:
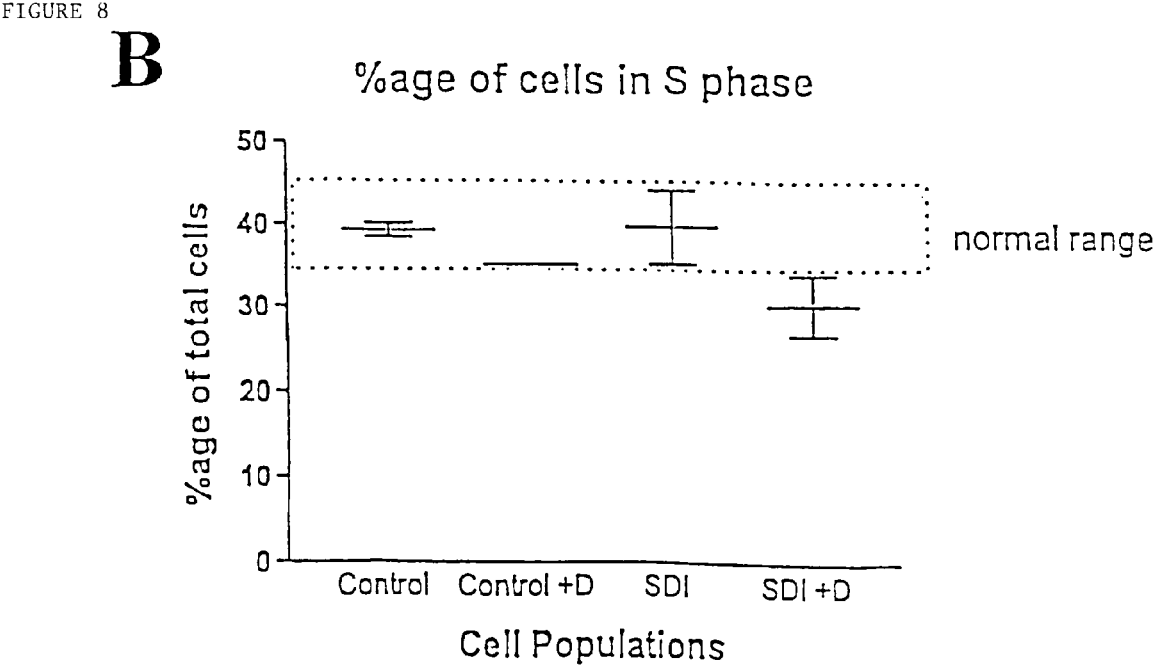

EJ cells grown in the absence of presence of Dex show no significant difference in the percentage of cells in $G_0$, $G_1$, irrespective of whether the cells were serum starved (cf; 45.4% and 52.4%) or grown normally. In contrast the representative FJ SDI-1 clone 7 showed significantly more cells in $G_0$, $G_1$, when grown in the presence of Dex after serum starvation (61%) than in the absence of SDI-1 expression (50.6%). Similar significant differences were observed even when the cells were not previously serum starved and treated with Dex as compared to nontreated cells. The mean percentage of cells in $G_0$, $G_1$, in different experiments is shown in FIG. 8A. Whereas both Dex treated and nontreated control cells as well as untreated SDI-1 vector infected cells all had between 40 and 53% of their cells in $G_0$, $G_1$, SDI-1 vector infected cells treated with Dex and thus expressing SDI-1 has between 55 and 62% in $G_0$, $G_1$. A commensurate reduction from 35–45% to 25–34% of the number of cells in the S phase could also be observed after Dex induction of SDI-1 expression (FIG. 8B). These results suggest that, irrespective of serum starvation, the induction of SDI-1 expression leads to an increased proportion of the cells in the $G_0$, $G_1$, phase of the cell cycle.

EXAMPLE 6

A second therapeutic use of SDI-1 involves the expression of an antisense SDI-1 to reduce the expression of endogenous SDI-1. This will prevent cells pausing to check DNA integrity and repair of the DNA before new DNA synthesis begins in preparation for the next cell division. If cells expressing antisense SDI-1 are treated with DNA damaging agents such as mutagens, carcinogens or irradiation (e.g. gamma, U.V.), the efficiency of DNA damage repair will be severely reduced because the cell will not pause to permit proof reading and repair. These cells will accumulate so much DNA damage that they are no longer viable.

Construction of ProCon IDS retroviral vector

Figure 9:
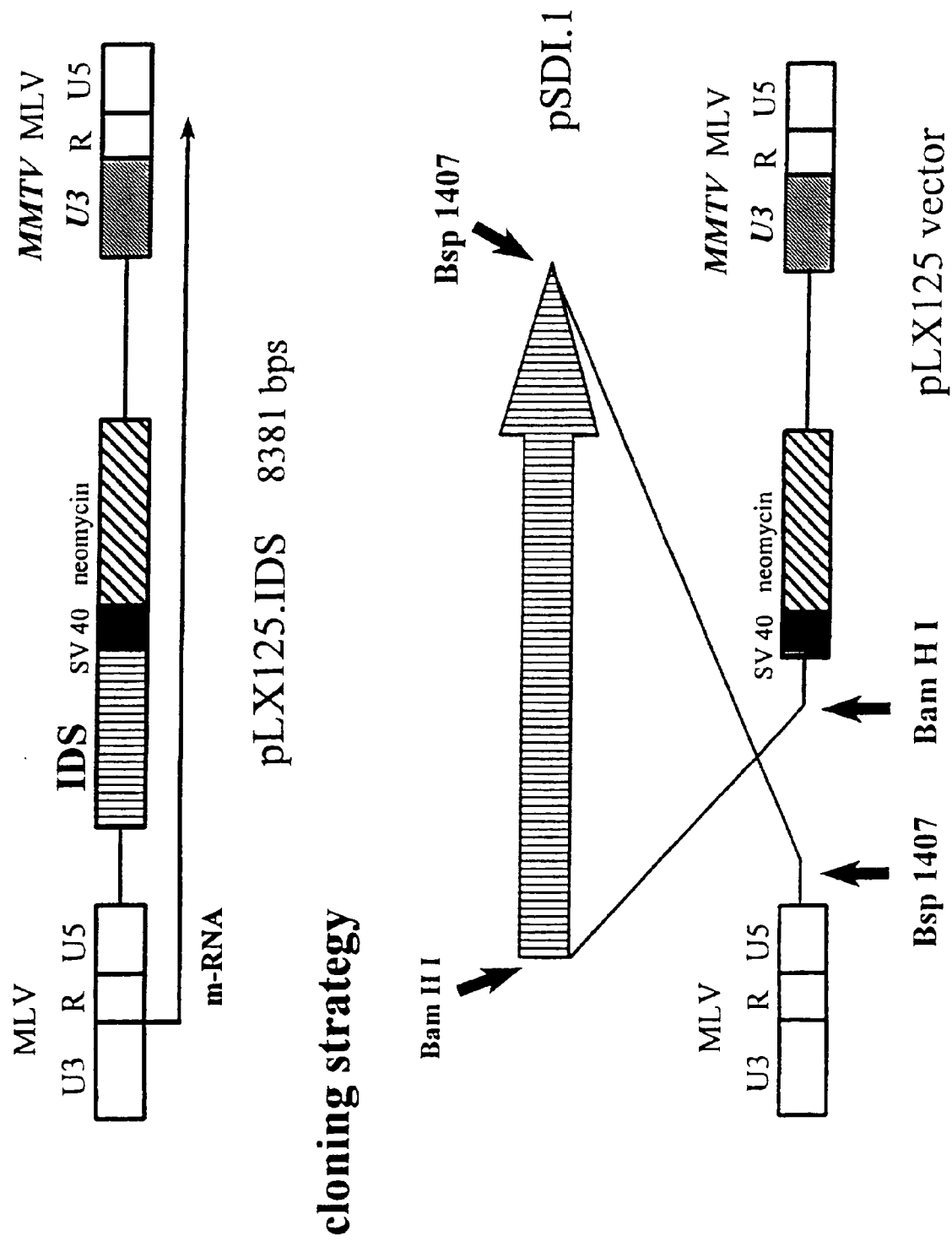
FIG. 9: Retroviral vector cloning strategy for pLX125.IDS.

The human SDI-1 CDNA carried in the plasmid pSDI-1 (5071 bp) (Noda, A., et al., *Exp. Cell. Res.*, 211:90–98 (1994)) was isolated by digestion with BamHI and Bsp 1407 (707 bp) and cloned in the antisense orientation (sticky ends) in the plasmid pLX125 (7812 bp) carrying U3 region of MMTV in place of the MLV U3 after digestion also with BamHI and Bsp 1407 (7674 bp) (sticky ends). The resulting plasmid was named pLX125.IDS (8381 bp) (FIG. 9).

pLX125 was prepared by ligation (sticky ends) of a 3545 bp AflIII BamHI fragment of pLXSN (Miller, A. D., & Rosman, G. J., *Biotechniques*, 7:980–990 (1989)) and a 4263 bp AflII BamHI fragment of p125.6 (Example 2, FIGS. 4A–4B). The resulting AflIII/AflIII fragment was blunt ended with klenow and ligated to give the plasmid pLX125 (7812 bp).

EXAMPLE 7

Transfection and Infection

For packaging, transfection and infection experiments, the human bladder carcinoma derived cell line EJ, cat kidney derived CK and PA317 retrovirus packaging cells were cultured in Dulbecco's modified Eagle's medium (DMEM) containing 10% fetal calf serum (FCS).

The packaging cells PA317 were seeded in a six well plate at a density of $5 \times 10^5$ cells one day prior to lipofection and then lipofected with 1 mg of plasmid pLX125.IDS and 1 mg of PHCMV-G using the lipofectamine kit from GIBCO/BRL according to the manufacturer's instructions (125IDS PA317).

Infections were performed essentially as described previously. Briefly, 48 hr conditioned cell culture medium from these 125IDS PA3178 cells was passed through 0.45 m Millipore filters, polybrene added to a final concentration of 8 mg/ml and 2 ml used to infect $5 \times 10^5$ EJ/CK cells in a 10 cm culture dish. After 5 hrs incubation, 6 ml of medium was added and the cells cultured overnight. The cells were then trypsinised and diluted 1:20. After 24 hrs the cell culture medium was changed to DMEM+10% FCS containing 800 mg/ml G418 for the EJ cells, 400 mg/ml G418 for the CK cells and 14 days later resistant cell clones as well as populations were isolated.

For transfections $5 \times 10^6$ CK or EJ cells were seeded in a 6 cm dish 24 hrs prior to transfection and then transfected with 10 mg of plasmid using the transfection kit from Pharmacia according to the manufacturer's instructions. After incubation for 14 hrs the cell was trysinised and diluted 1:5. After 24 hrs the cell culture medium was changed to DMEM containing 400 mg/ml G418 for the CK cells, 800 mg/ml G418 for the EJ cells and 14 days later resistant cell clones as well as populations were isolated.

EXAMPLE 8

Growth Properties of Transfected Cells

Expression of IDS should prevent cells from stopping in the checkpoint and therefore the cells should progress through the cell cycle.

In order to test whether the induction of IDS expression is associated with enhanced proliferation, 5000 cells were placed in each well of a six well plate (Falcon) i DMEM containing 10% FCS either with or without 10-6 dexamethasone. After 7 days the cells were fixed in methanol: acetic acid (3:1) and stained with Giemsa (Fisher So-G-28).

Transfected CK cells showed increased growth, as compared to their nontreated counterparts. The slight increased proliferation with the LXI 25 vector shows a proliferative effect of transfections as has been previously observed (Günzberg, W. H., et al., Carcinogenesis, 9:1849–1856 (1988)).

EXAMPLE 9

A cell survival curve describes the relationship between the radiation dose and the proportion of cells that survive. The capability of a single cell to grow into a large colony, which can easily be seen wit the naked eye, is a convenient proof that it has retained its reproductive integrity. The loss of the ability as a function of radiation dose is described by the dose survival curve.

Cells from an actively growing stock culture are prepared into a suspension by the use of trypsin, which causes the cells to round up and detach from the surface of the culture vessel. The number of cells of this suspension is counted. In this way, for example, 100 individual cells may be seeded into a dish. If this dish is incubated for 2 weeks, each single cell will divide many times and form a colony that is easily visible with the naked eye, especially if it is fixed and stained. All cells comprising each colony are the progeny of a single ancestor. For a nominal 100 cells seeded into the dish, the number of colonies counted may be expected to be in the range of 50 to 90. Ideally, it should be 100, but it seldom is for a variety of reasons, including suboptimal growth medium, errors and uncertainties in counting the cell suspension, and the trauma of trypsination and handling. The term plating efficiency (PF) indicates the percentage of cells seeded that grow into colonies.

Plating Efficiency (PF)=colonies counted, cells seeded×100

When a parallel dish is sealed with cells, exposed to a dose of 0 to 10 Gy of gamma-rays, and incubated for 2 weeks before being fixed and stained, then the following may be observed: (1) some of the seeded single cells are still single and have not divided; (2) some cells have managed to complete one or two divisions to form a tiny abortive colony; and (3) some cells have grown into large colonies that differ little from the unirradiated controls, although they may vary more in size. In general, the surviving fraction is given by surviving fraction (SF)=colonies gamma-ray counted cells seeded×(PF/100).

Cell survival curves

Plating efficiency (PE): EJ, CK cells and infected or transfected cell populations were seeded at different cell densities in 50 ml flasks (Nune, Denmark), (EJ and CK cells were cultured in DMEM containing 10% FS, CK transfectants in DMEM containing 10% FCS and 400 mg ml G418; Infected EJ cell clones in DMEM containing 10% FCS and 800 mg ml G418.)

After two weeks incubation the cells were fixed in methanol:acetic acid (3:1), stained with Giemsa (Fischer So-G-28) and colonies were counted. Cell culture flasks were seeded with the number of cells that give around 70 colonies after two weeks incubation and exposed to different doses of gamma-ray irradiation (1-10 Gy, 1 Gy=100 rads). Two weeks later the cell colonies were fixed and stained. Colonies were counted and the surviving fraction (SF) was determined.

Figure 10:
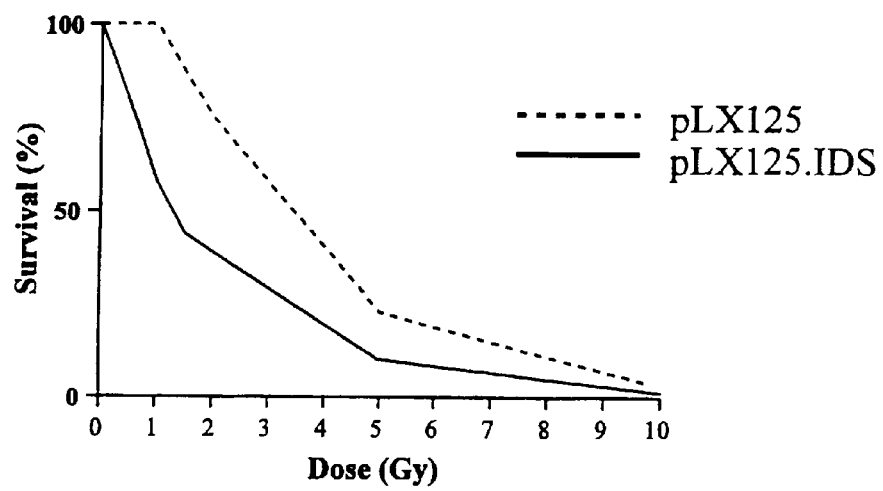
FIGS. 10A–10C: Survival of cells expressing antisense SDI-1 after radiation.
Figure 10:
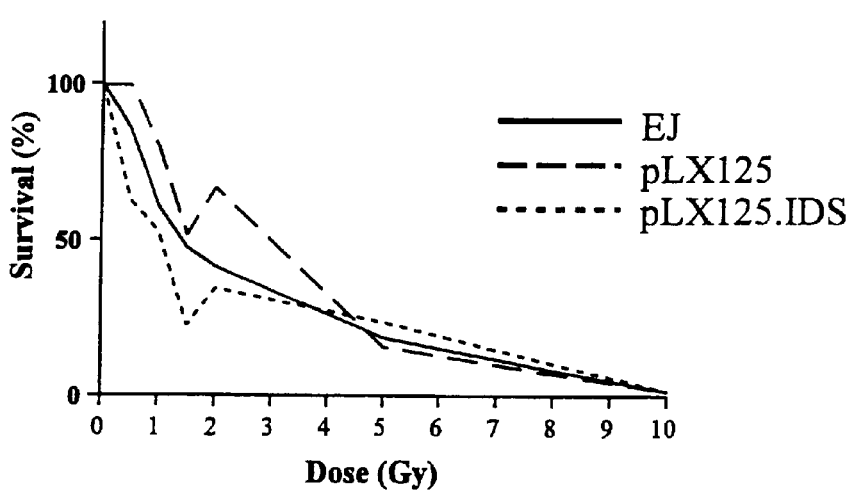
Figure 10:
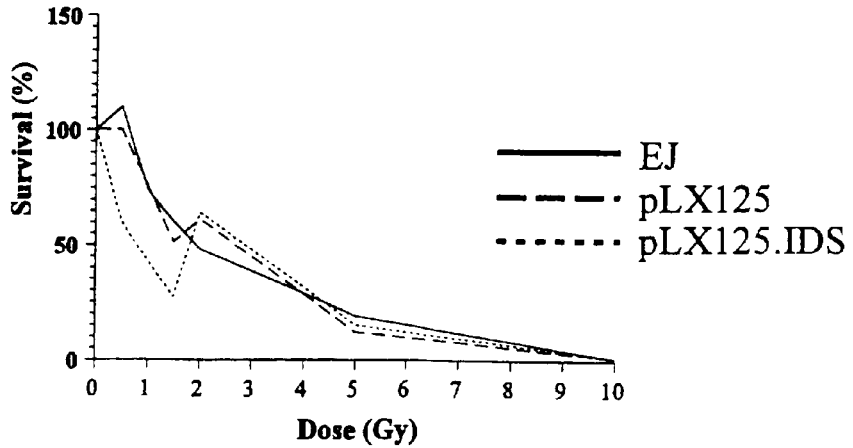

The graphs (FIGS. 10A–10C) show a decreased survival for the LX125.IDS transfected as well for the LX125.IDS infected cells in comparison to the parental cells and the transfected or infected cells with the LX125 vector alone, especially after irradiation with a dose till 1.5 Gy.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for producing a recombinant retroviral particle encoding an SDI-1 polypeptide or a fragment thereof, wherein the SDI-1 polypeptide or fragment thereof inhibits cell proliferation, the method comprising:
   (a) stably transfecting an isolated producer cell line with a retroviral vector comprising in 5' to 3' order:
      (1) a 5' LTR;
      (2) a nucleic acid sequence encoding an SDI-1 polypeptide or fragment thereof, wherein said SDI-1 polypeptide or fragment thereof inhibits cell prolfieration; and
      (3) a 3' LTR region comprising a complete or partial U3 deletion and an insertion in place thereof, wherein said insertion comprises a polylinker sequence into which a regulatory element or a promoter has been cloned; and
   (b) producing said recombinant retroviral particle in said stably transfected isolated producer cell line, wherein said retroviral particle encodes said SDI-1 polypeptide or fragment thereof, and further wherein said regulatory element or promoter becomes operatively linked to said nucleic acid sequence and regulates expression of said nucleic acid sequence upon infection of a target cell by said recombinant retroviral particle.

2. The method of claim 1 wherein the retroviral vector comprises a DNA sequence encoding SDI-1.

3. The method of claim 2, wherein the DNA sequence encoding an SDI-1 polypeptide or fragment thereof is under transcriptional control of a regulatory element selected from the group consisting of a target cell specific regulatory element, a target cell specific promoter, and an X-ray inducible promoter.

4. The method of claim 3 wherein the regulatory element is selected from the group consisting of a Whey Acidic Protein (WAP) regulatory element and a more mammary tumor virus (MMTV) regulatory element.

5. The method of claim 4 wherein the retroviral vector is pLXS-SDI1.

6. The method of claim 1, wherein the fragment comprises amino acids 1 to 71 of human SDI-1.

7. The method of claim 1, wherein the fragment comprises amino acids 42 to 58 of human SDI-1.

8. A recombinant retroviral particle produced by the method of claim 1.

9. A pharmaceutical composition comprising the retroviral particle of claim 8 and a pharmaceutically acceptable carrier or diluent.

10. An isolated producer cell line stably transfected with a retroviral vector encoding an SDI-1 polypeptide or a fragment thereof, said retroviral vector comprising in 5' to 3' order:
   (a) a 5' LTR;
   (b) a nucleic acid sequence encoding an SDI-1 polypeptide or fragment thereof, wherein said SDI-1 polypeptide or fragment thereof inhibits cell proliferation; and
   (c) a 3' LTR region comprising a complete or partial U3 deletion and an insertion in place thereof, wherein said insertion comprises a polylinker sequence into which a regulatory element or a promoter has been cloned, such that said regulatory element or promoter becomes operatively linked to said nucleic acid sequence and regulates expression of said nucleic acid sequence upon infection of a target cell by a recombinant retroviral particle produced by said isolated producer cell line.

11. The isolated producer cell line of claim 10, wherein the isolated producer cell line is a human cell line.

12. A pharmaceutical composition comprising the isolated producer cell line of claim 10 and a pharmaceutically acceptable carrier or diluent.

13. A method for introducing a DNA sequence encoding an SDI-1 polypeptide or fragment thereof into a human cell in vitro, the method comprising infecting the human cell with a retroviral particle produced by the isolated producer cell line of claim 10.

14. A method for treating a subject having a tumor or restenosis, the method comprising administering into said tumor or a site of restenosis of said subject a therapeutically effective amount of a recombinant retroviral particle produced by the isolated producer cell line of claim 10.

15. The method according to claim 14 wherein the administering is by injection of the recombinant retroviral particle into said tumor or said site of restenosis of said subject.

16. A method for producing a recombinant retroviral particle comprising an RNA sequence encoding an SDI-1 polypeptide that inhibits cell proliferation, the method comprising:

(a) stably transfecting an isolated producer cell line with a retroviral vector comprising in 5' to 3' order:
(1) a 5' LTR;
(2) a nucleic acid sequence encoding an SDI-1 polypeptide that inhibits cell proliferation; and
(3) a 3' LTR region comprising a complete or partial U3 deletion and an insertion in place thereof, wherein said insertion comprises a polylinker sequence into which a regulatory element or a promoter has been cloned; and
(b) producing said recombinant retroviral particle in said stably transfected isolated producer cell line, wherein said retroviral particle comprises said RNA sequence encoding said SDI-1 polypeptide, and further wherein said regulatory element or promoter becomes operatively linked to said nucleic acid sequence and regulates expression of said nucleic acid sequence upon infection of a target cell by said recombinant retroviral particle.

17. The method of claim 16 wherein the regulatory element or promoter is selected from the group consisting of a target cell specific regulatory element, a target cell specific promoter, and an X-ray inducible promoter.

18. The method of claim 17 wherein the regulatory element is selected from the group consisting of a Whey Acidic Protein (WAP) regulatory element and a mouse mammary tumor virus (MMTV) regulatory element.

19. The method of claim 18 wherein the retroviral vector is pLXS-SDI1.

20. An isolated producer cell line stably transfected with a retroviral vector encoding an SDI-1 polypeptide that inhibits cell proliferation, said retroviral vector comprising in 5' to 3' order:
(a) a 5' LTR;
(b) a nucleic acid sequence encoding an SDI-1 polypeptide that inhibits cell proliferation; and
(c) a 3' LTR region comprising a complete or partial U3 deletion and an insertion in place thereof, wherein said insertion comprises a polylinker sequence into which a regulatory element or a promoter has been cloned, wherein said regulatory element or promoter becomes operatively linked to said nucleic acid sequence and regulates expression of said nucleic acid sequence upon infection of a target cell by a recombinant retroviral particle produced by said isolated producer cell line.

21. The isolated producer cell line of claim 20, wherein the isolated producer cell line is a human cell line.

22. A method for introducing a DNA sequence encoding an SDI-1 polypeptide into a human cell in vitro, the method comprising infecting the human cell with a retroviral particle produced by the isolated producer cell line of claim 20.

23. A method for producing a recombinant retroviral particle comprising an RNA sequence encoding amino acids 1 to 71 of human SDI-1, the method comprising:
(a) stably transfecting an isolated producer cell line with a retroviral vector comprising a DNA sequence encoding amino acids 1–71 of human SDI-1, wherein:
(i) amino acids 1–71 of human SDI-1 inhibit cell proliferation; and
(ii) said producer cell comprises at least one DNA construct encoding a protein required for retroviral packaging; and
(b) producing said recombinant retroviral particle in said stably transfected isolated producer cell line.

24. An isolated producer cell line stably transfected with a retroviral vector encoding amino acids 1–71 of human SDI-1, said retroviral vector comprising in 5' to 3' order:
(a) a 5' LTR;
(b) a nucleic acid sequence encoding amino acids 1–71 of human SDI-1, wherein said amino acids 1–71 of human SDI-1 inhibit cell proliferation; and
(c) a 3' LTR region comprising a complete or partial U3 deletion and an insertion in place thereof, wherein said insertion comprises a polylinker sequence into which a regulatory element or a promoter has been cloned, wherein said regulatory element or promoter becomes operatively linked to said nucleic acid sequence and regulates expression of said nucleic acid sequence upon infection of a target cell by a recombinant retroviral particle produced by said isolated producer cell line.

25. A method for introducing a DNA sequence encoding a polypeptide comprising amino acids 1–71 of human SDI-1 into a human cell in vitro, the method comprising infecting the human cell with a retroviral particle produced by the isolated producer cell line of claim 24.

26. A method for producing a recombinant retroviral particle comprising an RNA sequence encoding amino acids 42 to 58 of human SDI-1, the method comprising:
(a) stably transfecting an isolated producer cell line with a retroviral vector comprising a DNA sequence encoding amino acids 42–58 of human SDI-1, wherein:
(i) amino acids 42–58 of human SDI-1 inhibit cell proliferation; and
(ii) said producer cell comprises at least one DNA construct encoding a protein required for retroviral packaging; and
(b) producing said recombinant retroviral particle in said stably transfected isolated producer cell line.

27. An isolated producer cell line stably transfected with a retroviral vector encoding amino acids 42–58 of human SDI-1, said retroviral vector comprising in 5' to 3' order:
(a) a 5' LTR;
(b) a nucleic acid sequence encoding amino acids 42–58 of human SDI-1, wherein said amino acids 42–58 of human SDI-1 inhibit cell proliferation; and
(c) a 3' LTR region comprising complete or partial U3 deletion and an insertion in place thereof, wherein said insertion comprises a polylinker sequence into which a regulatory element or a promoter has been cloned, wherein said regulatory element or promoter becomes operatively linked to said nucleic acid sequence and regulates expression of said nucleic acid sequence upon infection of a target cell by a recombinant retroviral particle produced by said isolated producer cell line.

28. A method for introducing a DNA sequence encoding a polypeptide comprising amino acids 42–58 of human SDI-1 into a human cell in vitro, the method comprising infecting the human cell with a retroviral particle produced by the isolated producer cell line of claim 27.

* * * * *